(12) United States Patent
Rice et al.

(10) Patent No.: US 7,555,332 B2
(45) Date of Patent: *Jun. 30, 2009

(54) FLUORESCENT LIGHT TOMOGRAPHY

(75) Inventors: Bradley W. Rice, Danville, CA (US); Chaincy Kuo, Oakland, CA (US); Daniel G. Stearns, Mountain View, CA (US); Heng Xu, Alameda, CA (US)

(73) Assignee: Xenogen Corporation, Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/829,927

(22) Filed: Jul. 29, 2007

(65) Prior Publication Data

US 2008/0031494 A1      Feb. 7, 2008

Related U.S. Application Data

(63) Continuation of application No. 11/733,358, filed on Apr. 10, 2007, and a continuation-in-part of application No. 10/606,976, filed on Jun. 25, 2003.

(60) Provisional application No. 60/840,247, filed on Aug. 24, 2006, provisional application No. 60/395,357, filed on Jul. 16, 2002, provisional application No. 60/396,458, filed on Jul. 16, 2002, provisional application No. 60/396,313, filed on Jul. 16, 2002.

(51) Int. Cl.
  *A61B 6/03*   (2006.01)
  *A61B 6/12*   (2006.01)

(52) U.S. Cl. .......... 600/473; 600/407; 600/425; 600/431; 600/476; 382/128; 250/363.01

(58) Field of Classification Search ........... 600/407, 600/476; 250/363.01, 317
See application file for complete search history.

(56) References Cited

U.S. PATENT DOCUMENTS

| | | | |
|---|---|---|---|
| 4,687,325 | A | 8/1987 | Corby, Jr. |
| 4,687,352 | A | 8/1987 | Igi et al. |
| 4,773,097 | A | 9/1988 | Suzaki et al. |

(Continued)

FOREIGN PATENT DOCUMENTS

EP   1 016 419   7/2000

(Continued)

OTHER PUBLICATIONS

Achilefu et al., "Novel Receptor-Targeted Fluorescent Contrast Agents for In Vivo Tumor Imaging", Investigative Radiology, vol. 35(8), Aug. 200, pp. 479-485.

(Continued)

*Primary Examiner*—Long V Le
*Assistant Examiner*—Vani Gupta
(74) *Attorney, Agent, or Firm*—Beyer Law Group LLP

(57) ABSTRACT

Described herein are systems and methods for obtaining a three-dimensional (3D) representation of the distribution of fluorescent probes inside a sample, such as a mammal. Using a) fluorescent light emission data from one or more images, b) a surface representation of the mammal, and c) computer-implemented photon propagation models, the systems and methods produce a 3D representation of the fluorescent probe distribution in the mammal. The distribution may indicate—in 3D—the location, size, and/or brightness or concentration of one or more fluorescent probes in the mammal.

20 Claims, 14 Drawing Sheets

U.S. PATENT DOCUMENTS

| | | |
|---|---|---|
| 5,202,091 A | 4/1993 | Lisenbee |
| 5,205,291 A * | 4/1993 | Potter .................. 600/431 |
| 5,242,441 A | 9/1993 | Avitall |
| 5,319,209 A | 6/1994 | Miyakawa et al. |
| 5,334,193 A | 8/1994 | Nardella |
| 5,414,258 A | 5/1995 | Liang |
| 5,452,723 A | 9/1995 | Wu et al. |
| 5,584,872 A | 12/1996 | LaFontaine et al. |
| 5,594,253 A | 1/1997 | Bueno et al. |
| 5,636,299 A | 6/1997 | Bueno et al. |
| 5,637,874 A | 6/1997 | Hammamatsu |
| 5,650,135 A | 7/1997 | Contag et al. |
| 5,661,562 A | 8/1997 | Aharon |
| 5,672,881 A | 9/1997 | Striepeke et al. |
| 5,705,807 A | 1/1998 | Throngnumchai |
| 5,738,101 A | 4/1998 | Sappey |
| 5,746,210 A | 5/1998 | Benaron et al. |
| 5,807,262 A | 9/1998 | Papaioannou et al. |
| 5,812,310 A | 9/1998 | Stewart et al. |
| 5,818,587 A | 10/1998 | Devaraj et al. |
| 5,835,617 A | 11/1998 | Ohta et al. |
| 5,840,572 A | 11/1998 | Copeland |
| 5,865,754 A * | 2/1999 | Sevick-Muraca et al. .... 600/476 |
| 5,867,250 A | 2/1999 | Baron |
| 5,917,190 A | 6/1999 | Yodh et al. |
| 5,943,129 A | 8/1999 | Hoyt et al. |
| 5,953,446 A | 9/1999 | Opsal et al. |
| 5,963,658 A | 10/1999 | Klibanov et al. |
| 5,970,164 A | 10/1999 | Bamberger |
| 6,069,698 A | 5/2000 | Ozawa et al. |
| 6,108,576 A | 8/2000 | Alfano et al. |
| 6,175,407 B1 | 1/2001 | Sartor |
| 6,205,347 B1 | 3/2001 | Morgan et al. |
| 6,208,886 B1 | 3/2001 | Alfano et al. |
| 6,217,847 B1 | 4/2001 | Contag et al. |
| 6,219,566 B1 | 4/2001 | Weersink et al. |
| 6,242,743 B1 | 6/2001 | DeVito et al. |
| 6,252,623 B1 | 6/2001 | Lu et al. |
| 6,264,610 B1 | 7/2001 | Zhu |
| 6,267,477 B1 | 7/2001 | Karpol et al. |
| 6,321,111 B1 | 11/2001 | Perelman et al. |
| 6,332,087 B1 | 12/2001 | Svenson et al. |
| 6,364,829 B1 | 4/2002 | Fulghum |
| 6,373,557 B1 | 4/2002 | Mengel et al. |
| 6,373,568 B1 | 4/2002 | Miller et al. |
| 6,377,353 B1 | 4/2002 | Ellis |
| 6,381,302 B1 | 4/2002 | Berestov |
| 6,392,241 B1 | 5/2002 | Rushbrooke et al. |
| 6,394,965 B1 | 5/2002 | Klein |
| 6,403,947 B1 | 6/2002 | Hoyt et al. |
| 6,415,051 B1 | 7/2002 | Callari et al. |
| 6,429,943 B1 | 8/2002 | Opsal et al. |
| 6,529,627 B1 | 3/2003 | Callari et al. |
| 6,549,288 B1 | 4/2003 | Migdal et al. |
| 6,597,931 B1 | 7/2003 | Cheng et al. |
| 6,615,061 B1 | 9/2003 | Khalil et al. |
| 6,615,063 B1 * | 9/2003 | Ntziachristos et al. ...... 600/312 |
| 6,618,152 B2 | 9/2003 | Toida |
| 6,618,463 B1 | 9/2003 | Schotland et al. |
| 6,628,401 B2 | 9/2003 | Toida |
| 6,628,747 B1 | 9/2003 | Schotland et al. |
| 6,636,755 B2 | 10/2003 | Toida |
| 6,642,953 B1 | 11/2003 | Nieto Velasco et al. |
| 6,646,678 B1 | 11/2003 | Kobayashi |
| 6,665,072 B2 | 12/2003 | Hoyt |
| 6,690,466 B2 | 2/2004 | Miller et al. |
| 6,690,520 B1 | 2/2004 | Kusuzawa |
| 6,693,710 B1 | 2/2004 | Hoyt |
| 6,710,770 B2 | 3/2004 | Tomasi et al. |
| 6,750,964 B2 | 6/2004 | Levenson et al. |
| 6,775,349 B2 | 8/2004 | Schotland et al. |
| 6,775,567 B2 | 8/2004 | Cable |
| 6,813,030 B2 | 11/2004 | Tanno |
| 6,919,919 B2 | 7/2005 | Nelson et al. |
| 6,924,893 B2 | 8/2005 | Oldenbourg et al. |
| 6,963,375 B1 | 11/2005 | Lundberg |
| 7,113,217 B2 * | 9/2006 | Nilson et al. ............... 348/373 |
| 7,184,047 B1 | 2/2007 | Crampton |
| 7,263,157 B2 | 8/2007 | Bruder et al. |
| 2002/0001080 A1 | 1/2002 | Miller |
| 2003/0002028 A1 | 1/2003 | Rice et al. |
| 2003/0099329 A1 | 5/2003 | Schotland et al. |
| 2004/0010192 A1 | 1/2004 | Benaron et al. |
| 2004/0015062 A1 | 1/2004 | Ntziachristos et al. |
| 2004/0021771 A1 | 2/2004 | Stearns et al. |
| 2004/0027659 A1 | 2/2004 | Messerschmidt et al. |
| 2004/0085536 A1 | 5/2004 | Schotland et al. |
| 2004/0262520 A1 | 12/2004 | Schotland et al. |
| 2005/0149877 A1 | 7/2005 | Rice et al. |
| 2005/0283071 A1 | 12/2005 | Ripoll et al. |
| 2006/0118742 A1 | 6/2006 | Levenson et al. |
| 2006/0119865 A1 | 6/2006 | Hoyt et al. |
| 2006/0146346 A1 | 7/2006 | Hoyt |
| 2006/0173354 A1 | 8/2006 | Ntziachristos et al. |
| 2006/0203244 A1 | 9/2006 | Nilson et al. |
| 2006/0245631 A1 | 11/2006 | Levenson |
| 2006/0268153 A1 | 11/2006 | Rice et al. |
| 2007/0016078 A1 | 1/2007 | Hoyt et al. |

FOREIGN PATENT DOCUMENTS

| | | |
|---|---|---|
| JP | 06-129984 | 5/1994 |
| JP | 08-136448 | 5/1996 |
| JP | 11-173976 | 7/1999 |
| WO | 96/16596 | 6/1996 |
| WO | WO97/40381 | 10/1997 |
| WO | WO98/34533 | 8/1998 |
| WO | WO 00/17643 | 3/2000 |
| WO | WO00/36106 | 6/2000 |
| WO | WO00/54581 | 9/2000 |
| WO | WO01/18225 | 3/2001 |
| WO | WO01/63247 | 8/2001 |
| WO | WO02/41760 | 5/2002 |

OTHER PUBLICATIONS

Arridge, "Photon-Measurement Density Functions. Part 1: Analytical Forms", Applied Optics, vol. 34, No. 31, 1, 1995, pp. 7395-7409.

Arridge, "Photon-Measurement Density Functions. Part 2: Finite-Element-Method Calculations", Applied Optics, vol. 34, No. 34, Dec. 1, 1995, pp. 8026-8037.

Australian Office Action dated Jul. 25, 2006 for Australian Application No. 2002303819.

Becker et al., "receptor-Targeted Optical Imaging of Tumors with Near-Infrared Fluorescent Ligands", Nature Biotechnology, vol. 19, Apr. 2001, pp. 327-330.

Benaron, David A., "A System for Imaging Infection and Gene Expression in the Body in 3-D," Biomedical Optical Spectroscopy and Diagnostics, 1998 Technical Digest, 1998, Optical Society of America, pp. 134-135.

Bevilacqua et al., "In Vivo Local Determination of Tissue Optical Properties: Applications to Human Brain", Applied Optics, vol. 38, No. 22, Aug. 1, 1999, pp. 4939-4950.

Bevilacqua et al., "Monte Carlo Study of Diffuse Reflectance at Source-Detector Separations Close to One Transport Mean Free Path", Optical Society of America, vol. 16, No. 12, Dec. 1999, pp. 2935-2945.

Bouvet et al., "Real-Time Optical Imaging of Primary Tumor Growth and Multiple Metastatic Events in a Pancreatic Cancer Orthotopic Model", Cancer Research, vol. 62, Mar. 1, 2002, pp. 1534-1540.

Chang et al., "Improved Reconstruction Algorithm for Luminescence Optical Tomography When Background Lumiphore is Present", Applied Optics, vol. 37, No. 16, Jun. 1, 1998, pp. 3547-3552.

Cheong et al., "A review of the Optical Properties of Biological Tissues", IEEE Journal of Quantum Electronics, vol. 26, No. 12, Dec. 1990, pp. 2166-2185.

Contag et al., "Photonic Detection of Bacterial Pathogens in Living Hosts", Molecular Microbiology, vol. 18, No. 4, 1995, pp. 593-603.

Contag et al., "Use of Reporter Genes for Optical Measurements of Neoplastic Disease In Vivo", Neoplasia, vol. 2, No. 1-2, Jan.-Apr. 2000, pp. 41-52.

EP Search Report dated Oct. 6, 2006 for EP Application No. EP 06 01 3492.

Eppstein et al., "Biomedical Optical Tomography Using Dynamic Parameterization and Bayesian Conditioning on Photon Migration Measurements", Applied Optics, vol. 38, No. 10, Apr. 1, 1999, pp. 2138-2150.

Francis et al, "Visualizing Pneumococcal Infections in the Lungs of Live Mice Using Bioluminescent *Streptococcus pneumoniae* Transformed with a Novel Gram-Positive lux Transponson", Infection and Immunity, vol. 69, No. 5, pp. 3350-3358.

Frohn, "Super-Resolution Fluorescence Microscopy by Structured Light Illumination," Dissertation submitted to the Swiss Federal Institute of Technology, Zurich, 2000.

Ghiglia et al., "Two-Dimensional Phase Unwrapping: Theory, Algorithms, and Software", Wiley-Interscience publication, 1998, ISBN 0-471-24935-1, p. 312.

Haskell et al., "Boundary Condition for the Diffusion Equation in Radiative Transfer", Optical Society of America, vol. 11, No. 10, Oct. 1994, pp. 2727-2741.

Hastings, "Chemistries and Colors of Bioluminescent Reactions: a Review", Gene, vol. 173, 1996, pp. 5-11.

Hawrysz et al., "Developments Toward Diagnostic Breast Cancer Imaging Using Near-Infrared Optical Measurements and Fluorescent Contrast Agents", Neoplasia, vol. 2, No. 5 Sep.-Oct. 2000, pp. 388-417.

Ishimaru, "Wave Propagation and Scattering in Random Media", vol. 1, Single Scattering and Transport Theory, Academic Press, 1978.

Ishimaru, "Wave Propagation and Scattering in Random Media", vol. 2, Multiple Scattering Turbulence Rough Surfaces and Remote Sensing, Academic Press, 1978.

Kienle, "Noninvasive Determination of the Optical Properties of Two-Layered Turbid Media", Applied Optics, vol. 37, No. 4, Feb. 1, 1998, pp. 779-791.

Mahmood et al., "Near-Infrared Optical Imaging of Protease Activity for Tumor Detection", Radiology, Dec. 1999, p. 866-870.

Maston (editor), "Biological Techniques: Fluorescent and Luminescent Probes for Biological Activity: A Practical Guide to Technology for Quantitative Real-Time Analysis", Second Edition, Academic Press, 1999.

Ntziachristos et al., "Experimental Three-Dimensional Fluorescence Reconstruction of Diffuse Media by Use of a Normalized Born Approximation", Optical Society of America, vol. 26, No. 12, Jun. 15, 2001, pp. 893-895.

Ntziachristos et al., "Fluorescence Molecular Tomography Resolves Protease Activity In Vivo", Nature Medicine, vol. 8, No. 7, Jul. 2002, pp. 757-760.

Office Action received in EP Application No. 03764754.2 dated Feb. 7, 2007.

Pickering et al., "Double-integrating-sphere system for measuring the optical properties of tissue," Applied Optics, Feb. 1, 1993, vol. 32, No. 4, pp. 399-410.

Prahl et al., "Determining the Optical Properties of Turbid Media by Using the Adding-Doubling Method", Applied Optics, vol. 32, No. 4, Feb. 1, 1993, pp. 559-568.

Rehemtulla et al., "Rapid and Quantitative Assessment of Cancer Treatment Response Using In Vivo Bioluminescence Imaging", Neoplasia, vol. 2, No. 6, 2000, pp. 491-495.

Research & Development (magazine), vol. 42, No. 9, Sep. 2000, Part 1 of 2.

Rice et al., "Advances in 2D In Vivo Optical Imaging Instrumentation," Abstract No. 186, Society for Molecular Imaging $2^{nd}$ Annual Meeting, Aug. 2003.

Rice et al., "In Vivo Imaging of Light-Emitting Probes", Journal of Biomedical Optics, vol. 6, No. 4, Oct. 2001, pp. 432-440.

Takeda et al., "Fourier-Transform Method of Fringe-Pattern Analysis for Computer-Based Topography and Interferometry", Optical Society of America, vol. 72, No. 1, Jan. 1982, pp. 156-160.

Toyooka et al., "Automatic Profilometry of 3-D Diffuse Objects by Spatial Phase Detection", Applied Optics, vol. 25, No. 10, May 15, 1986, p. 1630-1633.

Tromberg et al., "Properties of Photon Density Waves in Multiple-Scattering Media", Applied Optics, vol. 32, No. 4, Feb. 1, 1993, p. 607-616.

Tuchin, "Tissue Optics: Light Scattering Methods and Instruments for Medical Diagnosis", SPIE Press, 2000.

Weissleder et al., "In Vivo Imaging of Tumors with Protease-Activated Near-Infrared Fluorescent Probes", Nature Biotechnology, vol. 17, Apr. 1999, pp. 375-378.

Weissleder et al., "Shedding Light onto Live Molecular Targets", Nature Medicine, vol. 9, No. 1, Jan. 2003, p. 123-1218.

Windsor et al., "Imaging Pulmonary Inflammation Using Fluorescence Molecular Tomography," Society for Molecular Imaging, Sep. 23, 2005.

Wu et al., "Noninvasive Optical Imaging of Firefly Luciferase Reporter Gene Expression in Skeletal Muscles of Living Mice", Molecular Therapy, vol. 4, No. 4, Oct. 2001, pp. 297-306.

Yang et al., "Whole-Body Optical Imaging of Green Fluorescent Protein-Expressing Tumors and Metastases", PNAS, vol. 97, No. 3, Feb. 1, 2000, pp. 1206-1211.

Zhang et al., "Rapid In Vivo Functional Analysis of Transgenes in Mice Using Whole Body Imaging of Luciferase Expression", Transgenic Research, vol. 10, 2001, pp. 423-434.

Tauler et al., "Multivariate Curve Resolution Applied to Spectral Data from Multiple Runs of an Industrial Process," Analytical Chemistry, vol. 65, No. 15, Aug. 1, 1993, pp. 2040-2047.

Jaumot et al., "A graphical user-friendly interface fo MCR-ALS: a new tool for multivariate curve resolution in MATLAB," Chemometrics and Intelligent Laboratory Systems 76, 2005, pp. 101-110.

Wentzell et al., "Multivariate curve resolution of time course microarray data," BMC Bioinformatics 2006, 7:343, submitted Mar. 18, 2006, published Jul. 13, 2006.

Duponchel et al., "Multivariate curve resolution methods in imaging spectroscopy: influence of extraction methods and instrumental perturbations," J. Chem. Inf. Comput. Sci., vol. 43, No. 6, 2003, pp. 2057-2067.

Notice of Allowance dated Mar. 19, 2008 from U.S. Appl. No. 10/151,463.

European Examination Report dated Apr. 8, 2008 from EP Patent Application No. 06013492.1.

Chinese Office Action dated Apr. 4, 2008 from Chinese Patent Application No. 03821121.1.

Office Action dated Aug. 4, 2008 from U.S. Appl. No, 10/606,976.

Office Action dated Jun. 9, 2008 from Japanese Patent Application No. 2002-589773.

Office Action dated Aug. 6, 2008 from U.S. Appl. No. 11/733,358.

European Office Action dated Aug. 21, 2008 from EP Patent Application No. 03764754.2.

International Search Report dated Jul. 7, 2008 from PCT Application No. PCT/US08/59492.

Written Opinion dated Jul. 7, 2008 from PCT Application No. PCT/US08/59492.

Ntziachristos, Fluorescence Molecular Imaging, Annual Reviews of Biomedical Engineering, Aug. 2006, vol. 8, pp. 1-33.

* cited by examiner

FLUORESCENT LIGHT TOMOGRAPHY

CROSS-REFERENCE TO RELATED APPLICATIONS

This application is a continuation of U.S. application Ser. No. 11/733,358 filed Apr. 10, 2007, which claims priority under 35 U.S.C. §119(e) and is a non-provisional of U.S. Provisional Application No. 60/840,247, filed on Aug. 24, 2006 and titled "Fluorescent Imaging," by Rice et al.; the Ser. No. 11/733,358 patent application also claims priority under 35 U.S.C. § 120 and is a continuation-in-part of U.S. patent application Ser. No. 10/606,976, filed Jun. 25, 2003 and titled "Method and Apparatus for 3-D Imaging of Internal Light Sources," which claimed priority under 35 U.S.C. § 119(e) from a) U.S. Provisional Application No. 60/395,357, filed on Jul. 16, 2002 and titled "Method and Apparatus for 3-D Imaging of Internal Light Sources," by Stearns et al., b) U.S. Provisional Application No. 60/396,458, filed on Jul. 16, 2002 and titled "In Vivo 3D Imaging of Light Emitting Reporters," by Rice et al. and c) U.S. Provisional Application No. 60/396,313, filed on Jul. 16, 2002 and titled "3D in Vivo Imaging of Light Emitting Reporters," by Rice et al.; each of the above listed patent applications is incorporated by reference in its entirety for all purposes.

FIELD OF THE INVENTION

The present invention relates to imaging with light. In particular, the present invention relates to systems and methods for obtaining a three-dimensional representation of a fluorescent probe distribution within a scattering medium.

BACKGROUND OF THE INVENTION

Imaging with light is gaining popularity in biomedical applications. One currently popular light imaging application involves the capture of low intensity light from a biological sample such as a mouse or other small animal. This technology is known as in vivo optical imaging. A light emitting probe inside the sample indicates where an activity of interest might be taking place. In one application, cancerous tumor cells are labeled with light emitting reporters or probes, such as fluorescent proteins or dyes.

Photons emitted by fluorescent cells scatter in the tissue of the mammal, resulting in diffusive photon propagation through the tissue. As the photons diffuse, many are absorbed, but a fraction reaches the surface of the mammal—and can be detected by a camera. Light imaging systems capture images that record the two-dimensional (2D) spatial distribution of the photons emitted from the surface.

However, the desirable imaging information often pertains to the location and concentration of the fluorescent source inside the subject, particularly a three-dimensional (3D) characterization of the fluorescent source. Reliable techniques to convert the 2D information in the camera images to a 3D characterization of the fluorescent probe concentration are desirable.

SUMMARY OF THE INVENTION

The present invention provides systems and methods for obtaining a representation of a fluorescent light distribution inside an animal. The fluorescent light distribution can be used to indicate the presence and location of a fluorescent probe in the animal. Using a) fluorescent light emission data from one or more images, b) a surface representation of at least a portion of the animal, and c) a computer-implemented model for photon propagation in the animal, the systems and methods determine a representation of the fluorescent light distribution inside the animal. The distribution may indicate the location, size, concentration and/or brightness of one or more fluorescent probes in the animal.

In one embodiment, the present invention relates to a method for obtaining a three-dimensional representation of a fluorescent probe distribution located inside an animal. The method includes obtaining one or more fluorescent images of at least a portion of the animal. The method also includes obtaining a three dimensional representation of a surface portion of the animal. The method further includes mapping fluorescent image data from the one or more fluorescent images to the three dimensional representation of the surface portion of the animal to create fluorescent light emission data from the surface portion of the animal. The method additionally includes determining a three-dimensional representation of the fluorescent probe distribution internal to the animal using the fluorescent light emission data from the surface portion of the animal.

In another embodiment, multiple fluorescent images are captured. A first fluorescent image includes a first trans-illumination position for an excitation light source relative to a camera; a second fluorescent image includes a second trans-illumination position for the excitation light source relative to the camera In yet another embodiment, the three-dimensional imaging accommodates for autofluoresence in the animal being imaged. In this case, light imaging methods determine autofluoresence data in the animal and alter fluorescent light emission data from a surface of the animal with the autofluorescence data, before determining the three-dimensional representation of the fluorescent light distribution internal to the animal.

In still another embodiment, the present invention relates to an imaging system for obtaining a representation of a fluorescent probe distribution located inside an animal. The imaging system comprises an imaging chamber and a processing system. The imaging chamber includes a set of walls enclosing an interior cavity, a stage configured to support the animal within the interior cavity, a fluorescent excitation source, and a camera. The processing system includes a processor and memory. The memory includes instructions for obtaining one or more fluorescent images of at least a portion of the animal and instructions for obtaining a three dimensional representation of a surface portion of the animal. The memory also includes instructions for mapping fluorescent image data from the one or more fluorescent images to the three dimensional representation of the surface portion of the animal to create fluorescent light emission data from the surface portion of the animal. The memory further includes instructions for determining a three-dimensional representation of the fluorescent probe distribution internal to the animal using the fluorescent light emission data from the surface portion of the animal.

In another embodiment, the present invention relates to logic encoded in one or more tangible media for execution and, when executed, operable to obtain a three-dimensional representation of a fluorescent probe distribution located inside a mammal.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

Figure 1:
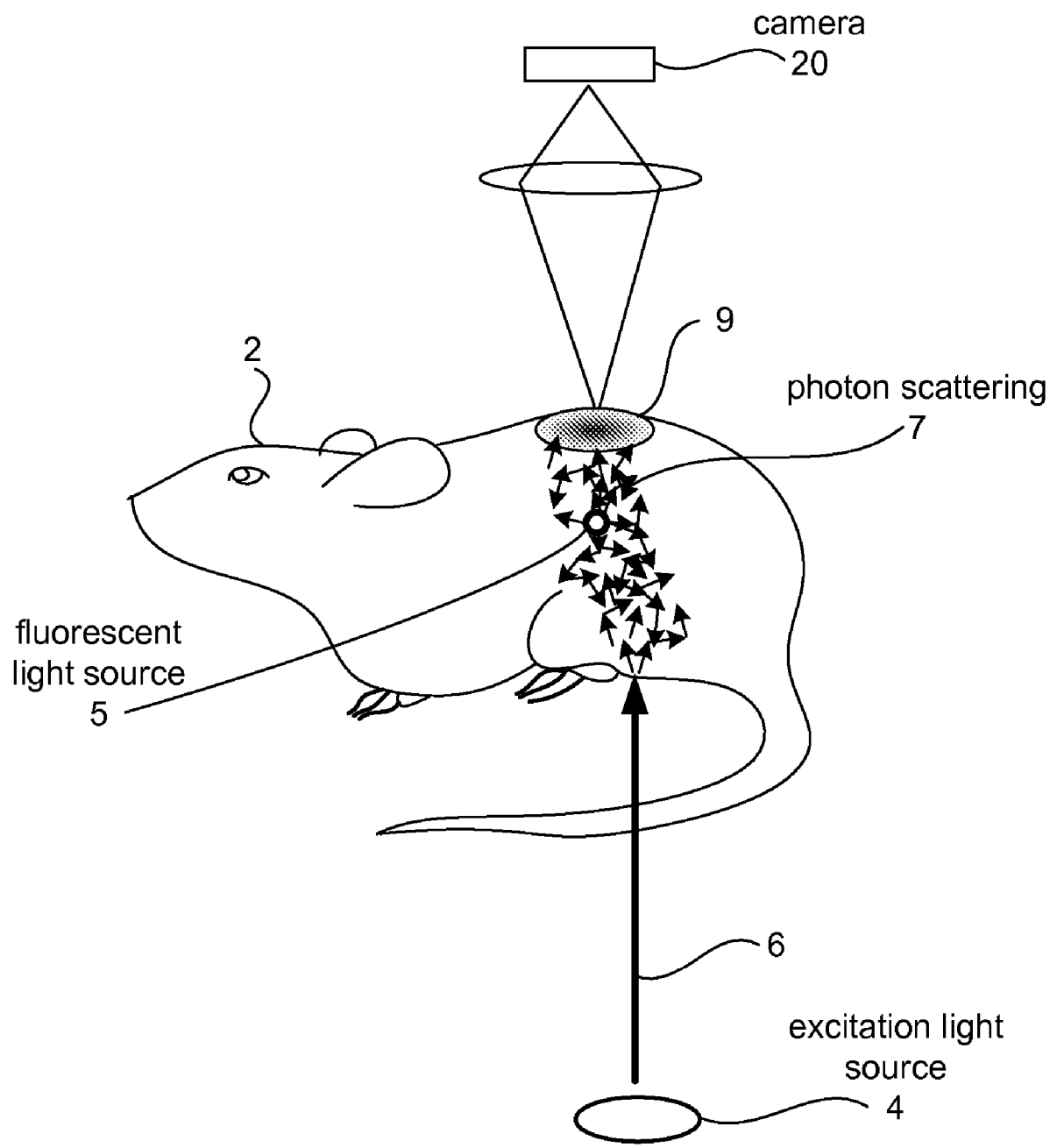
FIG. 1 shows a simplified pictorial of diffusive light propagation into, through, and out from, a mouse.

Systems and methods described herein obtain a three-dimensional (3D) representation of a fluorescent probe distribution inside a sample. This is referred to as fluorescent tomographic imaging. FIG. 1 shows a simplified pictorial of fluorescent light imaging in a mouse 2.

The fluorescent probe distribution may include light data that describes one or more of: an estimated light intensity of one or more fluorescent probes 5 in mouse 2, an estimated location of the one or more fluorescent probes 5, an estimated size or shape of a distribution of fluorescent probes 5, and/or spectral characteristics of the one or more fluorescent probes 5. In one embodiment, a single fluorescent probe 5 is reconstructed as a point. In another embodiment, the probe 5 is reconstructed as a complex structure with dimensions characterized spatially in 3D. Although the fluorescent light distribution in FIG. 1 shows a single probe 5, the mouse 2 may include multiple sites and fluorescent probes 5. For simplicity, the remaining discussion will mainly refer to a single internal fluorescent probe 5; it is understood that tomographic reconstruction and processing described herein is well suited for finding and reconstructing multiple fluorescent probes 5 in a mouse 2 or other object being imaged.

Fluorescent probe 5 generally refers to any object or molecule that produces fluorescent light. The fluorescent probe 5 absorbs incident energy of a certain wavelength or wavelength range and, in response, emits light energy at a different wavelength or wavelength range. The absorption of light is often referred to as the "excitation", while the emission of longer wave lights as the "emission". The output wavelength range is referred to herein as 'output spectrum'. Fluorescent probe 5 may include one or more fluorescent light emitting molecules, called 'flourophores'. A flourophore refers to a molecule or a functional group in a molecule that absorbs energy of a specific wavelength and re-emits energy at a different wavelength. Many commercially available fluorophores are suitable for use with mouse 2. Suitable fluorophores include Qdot® 605, Qdot® 800, AlexaFluor® 680 and AlexaFluor® 750 as provided by Invitrogen of San Diego, Calif. Both organic and inorganic substances can exhibit fluorescent properties, and are suitable for use with fluorescent probe 5. In one embodiment, fluorescent probe 5 emits light in the range of about 400 nanometers to about 1300 nanometers.

The fluorescent probe distribution may be internal to any of a variety of light-emitting objects, animals or samples that contain light-emitting molecules. Objects may include, for example, tissue culture plates and multi-well plates (including 96, 384 and 864 well plates). Animals including a fluorescent probe distribution may include mammals such as a human, a small mammal such as a mouse, cat, primate, dog, rat or other rodent. Other animals may include birds, zebra-fish, mosquitoes and fruit flies, for example. Other objects and samples are also suitable for use herein, such as eggs and plants. For ease of discussion, the remaining disclosure will show and describe a mouse 2 as an imaging object that contains a fluorescent probe.

Animal tissue is a turbid medium, meaning that photons are both absorbed and scattered as they propagate through tissue. FIG. 1 shows a simplified pictorial of diffusive light propagation into, through, and out from, mouse 2.

An excitation light source 4 produces incident light 6 that enters a portion of mouse 2. The incident light 6 scatters in the mouse tissues and some of it eventually reaches an internal fluorescent probe 5. When excited by incident light 6, fluorescent probe 5 emits fluorescent light 7 from within mouse 2. The fluorescent photons 7 scatter and travel through tissue in the mouse to one or more surfaces 9; the light emitted from the surface may then be detected by a camera 20.

Thus, as light 6 and 7 diffuses through the mouse, some of the light is absorbed, but a fraction of the light propagates to a surface that faces the camera 20. For fluorescent imaging, there is a two-stage diffusion: a) incident light 6 from an incident surface to fluorescent probe 5, and b) emitted fluorescent light 7 from fluorescent probe 5 to the one or more surfaces 9. Methods described herein model the light propagation in mouse 2 to determine 3D parameters of fluorescent probe 5 and solve for the internal fluorescent probe distribution 5—given images captured by the camera and the model.

A difficulty in tomographic imaging mice is that the complex surface of the mouse will change with each mouse, and potentially each time the mouse is imaged (as its position and body shifts). The probe may also change each time the mouse is imaged—in position, size, strength, and spectral distribution. The difficulty, then, is determining the 3D parameters of an internal fluorescent probe distribution, such as the 3D location, size and brightness distribution of fluorescent probe 5, given that many parameters needed for tomographic imaging may change with each trial.

One distinguishing feature of methods described herein is that they use an actual surface topography of the mouse—as it rests under a camera at the time that light images are captured—or any other time. In this case, the methods also employ topographic determination tools. Topographic imaging determines a surface representation of an object, or a portion thereof. In one embodiment, the present invention uses structured light to determine a surface topography for at least a portion of the mouse. Tomographic imaging refers to information inside the mouse surface. An exemplary illustration of topographic vs. tomographic imaging uses a 2D planar slice through the mouse: topography gives the surface (the outer bounding line), while tomography provides information inside the bounding surface.

Another challenge to tomographic reconstruction that is overcome herein: the tissue in mouse 2 also autofluoresces. Tissue autofluorescence may act as a source of background or noise to tomographic imaging of a fluorescent probe distribution, and techniques described below also a) model autofluorescence and b) separate the contributions of tissue autofluorescence from light emitted from the mouse surface. This isolates light emitted from the mouse surface that corresponds to fluorescent probe 5.

The present invention overcomes these difficulties and permits real-time fluorescent tomographic imaging, despite variability and complexity of the mouse surface, the effects of autofluorescence, or internal fluorescent probe distribution.

In one embodiment, simplifying approximations to a photon diffusion model are implemented in order to expedite the computation time required to perform a reconstruction of the light corresponding to fluorescent probe 5. With the approximations described below, reconstruction times of less than 5 minutes may be achieved—compared with hours or days for methods that use FEM or Monte Carlo modeling.

Figure 2:
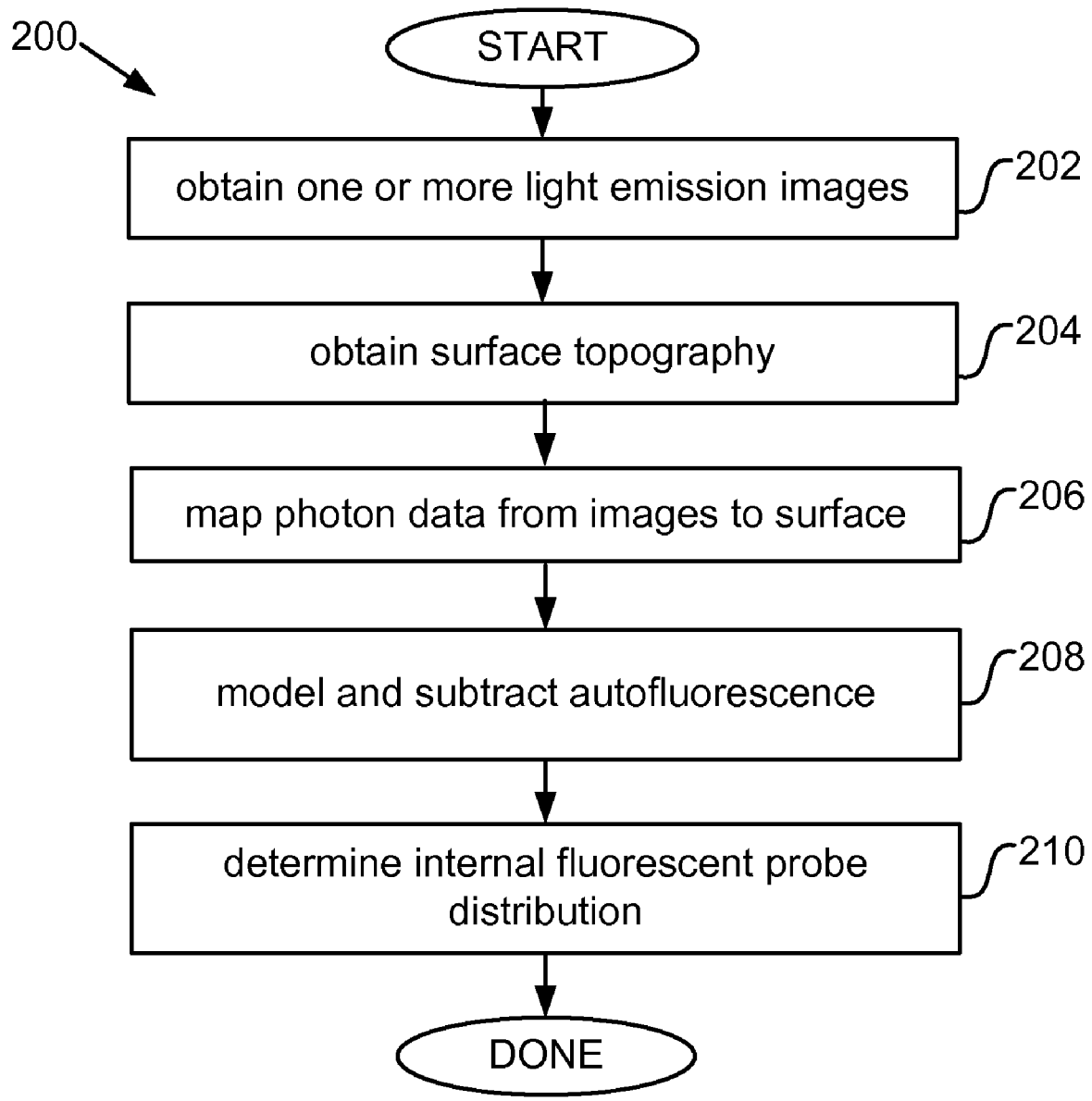
FIG. 2 illustrates a method for obtaining a 3D representation of a fluorescent probe distribution located inside a mammal in accordance with one embodiment of the present invention.

FIG. 2 illustrates a method 200 for obtaining a 3D representation of a fluorescent light distribution located inside a mouse in accordance with one embodiment of the present invention. Processes in accordance with the present invention may include up to several additional steps not described or illustrated herein in order not to obscure the present invention.

Figure 3:
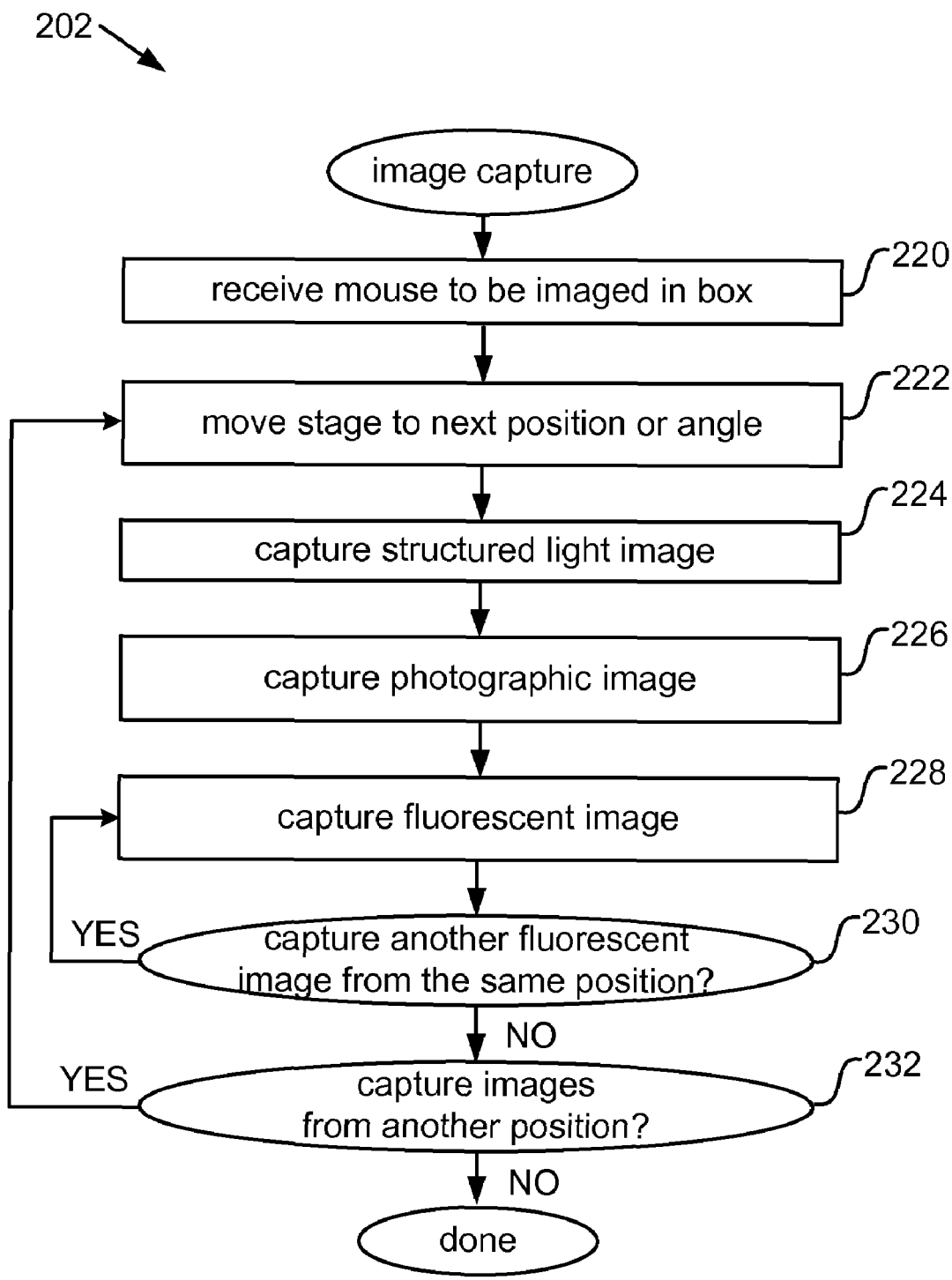
FIG. 3 shows a process flow for fluorescent image capture suitable for use in the method of FIG. 2.

Method 200 obtains one or more fluorescent images of at least a portion of the mouse (202). The images include fluorescent image data that describes fluorescent light emitted from the mouse. The images may be recalled from memory (previously captured) and/or captured in real time by a camera and imaging system, such as that described below with respect to FIGS. 14A and 14B. FIG. 3 describes one suitable method for image capture. In one embodiment, the fluorescent image data describes light that falls upon a camera or other photon detector that is distant from the mouse. In this case, the fluorescent image data is stored in the images in two-dimensions (2D).

Method 200 maps the 2D fluorescent image data onto a surface of the mouse (206). Before the mapping can occur, method 200 obtains a surface representation of at least a portion of the mouse (204). The surface portion may include all of the mouse, or a smaller portion. Typically, this portion includes parts of the mouse that the fluorescent image data will be mapped onto.

The surface representation refers to a mathematical description or approximation of the actual surface of the mouse, or a portion thereof. The surface representation need not include the entire mouse, and may include a portion of the mouse relevant to a particular imaging scenario. With a mouse for example, the surface representation might not necessarily include distal portions of the tail and distal portions of every foot. Thus, the surface representation is meant to broadly refer to any surface portion of the mouse and not necessarily the entire mouse. Typically, the surface representation includes one or more surface elements or regions of interest on the sample that produce surface light emission data related to the internal probe. For user convenience, the surface representation is often displayed in a pictorial depiction such as a 3D depiction (see FIGS. 13A and 13B).

Suitable techniques to obtain a surface representation include structured light, or another imaging modality such as computer tomography (CT) or magnetic resonance imaging (MRI), for example. The surface representation may be divided into a surface mesh comprising a set of surface elements, as will be described below.

In one embodiment, structured light is used to obtain a surface representation of the mouse. Structured light uses a set of lines of light that are projected down on the mouse at an angle (at about 30 degrees, for example) to the surface normal. The mouse generates structured light surface information as each light line reacts to the shape of the animal. Cumulatively, the lines of light each bend or alter in spacing as they pass over the mouse. The structured light surface information can be measured by a camera and used to determine the height of the surface at surface portions of the mouse that are illuminated by the structured light source. These surface portions are the portions of the mouse that face the camera (for a current position of the mouse relative to the camera). The position of the mouse relative to the camera may be changed to gain multiple structured light images and structured light information from multiple views.

A camera captures the structured light surface information, digitizes the information and produces one or more structured light images. A processor, operating from stored instructions, produces a 3D surface representation of the mouse—or a portion of the object facing the camera—using the structured light information. More specifically, a processing system, running on stored instructions for generating a topographic representation (a surface map) from the structured light surface information, builds a 3D topographic representation of the mouse using the structured light surface information. If multiple views are used, structured light topographies from these multiple views may be "stitched together" to provide a fuller surface representation from different angles. Structured light image capture, hardware and processing suitable for use with a mouse is described further in commonly owned and pending patent application Ser. No. 11/127,842 and entitled "Structured Light Imaging Apparatus", which is incorporated herein by reference in its entirety.

Once the surface topography is determined, process flow 200 maps the fluorescent image data in the 2D fluorescent images to fluorescent image data at a surface of the mouse (206). This converts 2D light data collected at a camera to 3D light data at a 3D surface of the mouse. In one embodiment, the mapping converts radiance data from the fluorescent images to photon density just inside the surface.

The mapping manipulates 2D camera data according to the geometry between the mouse surface and the camera lens to derive values of the light emission intensity (or radiance) at the surface. A variety of techniques can be used to map camera light data to the mouse surface. In one embodiment, the mapping uses a simple 3D translation based on the relative position between the camera and mouse surface. When the mouse rests on a stage in an imaging box, four spatial relationships between a camera and a stage that supports the mouse include: the camera and stage both do not move, the camera moves relative to the stage, the stage moves relative to the camera, and the camera and stage both move relative to each other. In any of these cases, the position of the camera relative to the stage/mouse is known. This permits a 3D translation using the known coordinates from the camera to the mouse surface.

Figure 5:
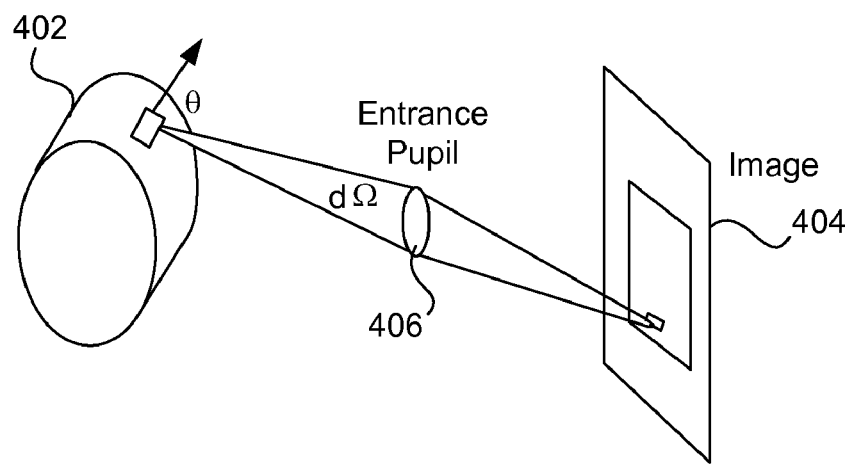
FIG. 5 illustrates a sample relationship for converting 2D camera data to surface data for a sample surface element.

More sophisticated spatial relationships between a camera and mouse may be used. In another embodiment, the angle of the mouse surface is also accounted for in the mapping. FIG. 5 illustrates a relationship for converting 2D camera data to surface data for a sample surface element 402. FIG. 5 shows a relationship between surface element 402 (on the mouse), image 404, and an entrance pupil or camera 406 of an imaging system. Light emitted from surface element 402 passes through entrance pupil 406 and is recorded in image 404. The angle of emission with respect to the surface normal is θ, which is known from the surface topography determined in 204. The entrance pupil 406 subtends a small solid angle dΩ. The imaging system may collect light emitted from surface element 402 on the sample at an angle θ (measured with respect to the normal to surface element 402) into the solid angle dΩ subtended by the entrance pupil. This information may then be used to convert image data obtained by the camera into the surface emission intensity corresponding to the surface geometry.

Emission of light from a mouse surface may be specified in units of radiance, such as photons/sec/cm$^2$/steradian. In one embodiment, an imaging system captures images of the mouse and reports surface intensity in units of radiance. Surface radiance can be converted to photon density just inside the mouse surface, using a model for photon propagation at the tissue-air interface, as described below. When the surface representation includes a set of surface elements, the mapping may produce a surface emission data vector that includes photon density at each surface element for the mouse topography. The photon density just inside the surface are then related to a light emitting probe distribution inside the mouse tissue using a diffusion model.

Returning back to FIG. 2, method 200 then models the contributions of tissue autofluorescence to the light emitted from the mouse (208). Autofluorescence refers to the natural fluorescence of substances within a material or organism. Mammalian tissue has autofluorescence properties that will affect fluorescent imaging. A camera receives image data that includes both: a) light escaping from the mouse surface due to autofluorescence of tissue in the mouse, and b) light escaping from the mouse surface due to fluorescent probe 5. From a camera's perspective, these two contributions are often mixed.

Multiple techniques are contemplated for determining autofluorescence and separating it from the surface emission for fluorescent probe 5. In one embodiment, autofluorescence is determined by measurements made in control animals (animals without a fluorescent probe). In this case, an average autofluorescence yield per unit volume of tissue can be derived from images of autofluorescence. The autofluorescence yield can then be used in a forward model of light propagation, e.g., see Eq. 7 below and its associated description.

Other autofluorescence determination techniques may be used. For example, when performing transillumination fluorescence measurements, the autofluorescence pattern on a surface of the animal typically matches a transillumination pattern observed when imaging with an emission filter and no excitation filter. This provides another way to determine and correct for autofluorescence. The process may include: 1) acquiring a normal fluorescence image with specified excitation filter and emission filter (image 250); 2) acquiring another image with excitation filter removed (image 252); multiplying image 252 by an appropriate scale factor and subtracting it from image A, thus reducing the contribution of autofluorescence from image A.

Another method to reduce autofluorescence is to use spectral unmixing. In this case, images are acquired with an array of different emission or excitation filters. Spectral unmixing software separates autofluorescence from the fluorescent probe emission, using known spectral characteristics of the images.

Figure 4:
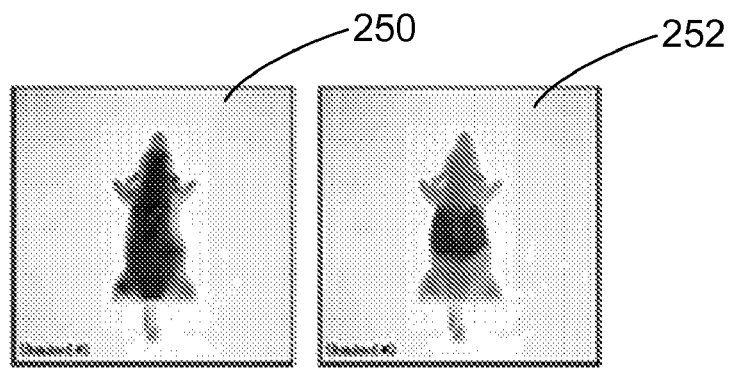
FIG. 4 shows sample images of: autofluorescence of a mouse, fluorescence of an internal probe in the mouse; and a combination of the fluorescence and autofluorescence.

After autofluorescence has been determined and separated from the surface emission data, the remaining fluorescent probe emission contributions to the surface emission data can be used for tomographic processing (without the noise and contributions of tissue autofluorescence). Method 200 subtracts the modeled tissue autofluorescence from the light emitted from the surface (as calculated in 206), which isolates the light/signal due to the fluorescent probe 5. This is shown pictorially in FIG. 4 with two epi-illumination images: image 250 shows the autofluorescence of a mouse; image 252 shows the fluorescence of the internal probe in the mouse.

Method 200 then calculates a 3D representation of the fluorescent probe distribution internal to the mouse (210). As the term is used herein, a fluorescent probe distribution refers to a description or mathematical depiction of fluorescent light emitters inside the mouse. Typically, the fluorescent light corresponds to a fluorescent probe disposed inside the animal. As mentioned above, the fluorescent probe may include a fluorescent marker such as a dye molecule, or a fluorescent reporter that produces fluorescent light based on gene expression.

Light data internal to the mouse 2 surface generally refers to mathematical representation or approximation of light within the mouse 2 interior. This may include a set of points or volume elements, each characterized by 3D position and a source strength. In one embodiment, the present invention divides the mouse 2 interior into volume elements where each volume element is considered to contain a point light source at its center. A solid mesh of these volume elements then defines a collection of point sources used to approximate light data internal to the mouse and the actual probe distribution within mouse 2. For example, a solid mesh of cubic volume elements may be used.

In one embodiment, fluorescent probe 5 includes emits low-intensity light. In one embodiment, a low intensity fluorescent probe of the present invention emits light within mouse in the range of about $10^4$ to about $10^{14}$ photons/second, depending on probe concentration and excitation light intensity. For some imaging systems, a fluorescent probe 5 that emits flux in the range of about $10^4$ to about $10^{10}$ photons/second is suitable. Other light fluxes are permissible with the present invention. Photons/second is one unit of measure suitable to quantify the amount of light produced by probe 5. Other units of measure are known to one of skill in the art, such as Watts. For reference, the conversion of photons/second to Watts is 3.3 nanowatts equals about $10^{10}$ photons/second at 600 nm. In one embodiment, probe 5 emits light between about $10^{-15}$ to $10^{-6}$ watts of light. The amount of light produced by fluorescent probe 5 refers to the light emitted within mouse 2—not necessarily the amount of light generated by excitation light source 4 (such as an LED) that generates the light incident on the fluorescent probe 5.

Method 200 uses the fluorescent light emission data from the mouse surface, along with tomographic imaging software that models light propagation internal to the mouse and solves for fluorescent probe distribution. The internal light propagation modeling includes both a) fluorescent excitation light propagation from the excitation light source 4, and its entry points into the mouse, to the fluorescent probe 5, and b) fluorescent emission light propagation from the fluorescent probe 5 to the surfaces captured in the fluorescent images.

Figure 13A:
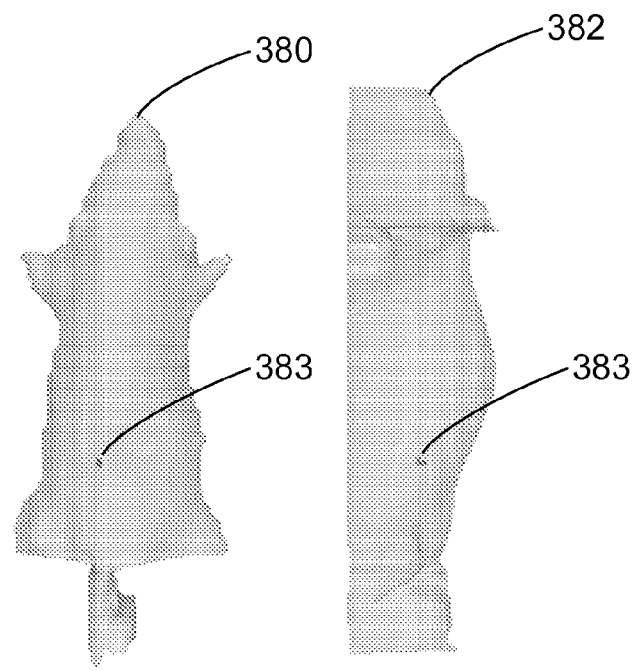
FIGS. 13A and 13B show sample reconstructed results for a fluorescent probe distribution within a phantom mouse and real mouse, respectively.
Figure 13B:
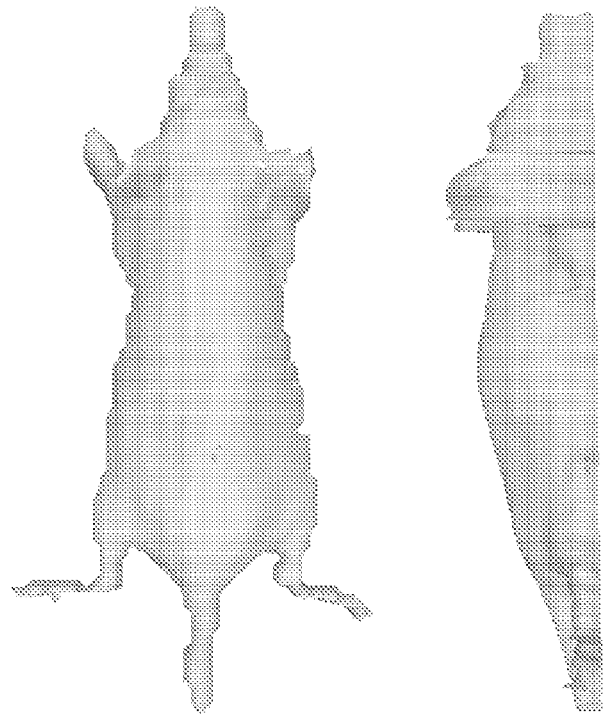

Tomographic modeling, processing, and fluorescent probe determination of step 210 is described in further detail below with respect to FIGS. 9 and 10. For user convenience, the resultant 3D representation produced by method 200 may be expressed as a pictorial depiction, e.g., on a computer monitor. FIGS. 13A and 13B show depictions of a mouse with a 3D surface topography and internal fluorescent probe 5 determined using method 200.

Tomographic imaging in method 200 finds use in a wide array of imaging and research applications such as oncology, infectious disease research, gene expression research, and toxicology, for example. The tomographic imaging is suitable for use with samples having a complex surface, such as a mouse. As the term is used herein, a complex surface is any surface that cannot be described solely using a single polygonal description. The reconstruction techniques described herein place no restrictions on the source distribution, such as the number of probes in the sample or the sizes and shapes of the sources, and no restrictions on the geometry, size or shape of the surface.

In some embodiments, method 200 may occur in real time where image capture (202), topographic acquisition (204) and the data calculations (204-210) all occur without significant delays to a user. In other words, soon after all the images are obtained—e.g., the images are captured or previously captured images are selected and recalled from memory—and the user inputs desired parameters for the tomographic assessment, method 200 outputs 3D details for the internal fluorescent probe 5. In one embodiment, mapping the fluorescent image data and determining the 3D fluorescent probe distribution (steps 206-210) finishes in less than about 5 minutes. In another embodiment, details of a fluorescent probe distribution are determined in less than about 1 minute. A video display may then show a pictorial representation of the tomographic reconstruction output on a monitor to a user. This quick processing allows a user to repeat process flow 200—or change parameters in the tomographic assessment relatively easily. This increases researcher productivity. If the mouse is in an imaging box and under anesthesia, this also permits multiple imaging sessions, in efficient succession, without a need to handle the mouse between tomographic imaging sessions. This real time imaging permits the mouse to be anesthetized for shorter durations (despite permitting multiple imaging sessions).

FIG. 3 shows a process flow for fluorescent image capture 202 (202 in FIG. 2) according to a specific embodiment of the present invention. In one embodiment, image capture 202 occurs with the mouse resting or lying on a horizontal stage or flat surface in a resting or normal position, without the need for any straps holding the mouse. The mouse may be anesthetized to prevent movement during imaging 202. The stage may then move between image captures, but the mouse typically remains stationary on the stage during image capture with the camera. In addition to fluorescent light image capture, process flow 202 also captures photographic and structured light images. Other embodiments of fluorescent light image capture 202 need not include photographic and structured light image capture.

Figure 14A:
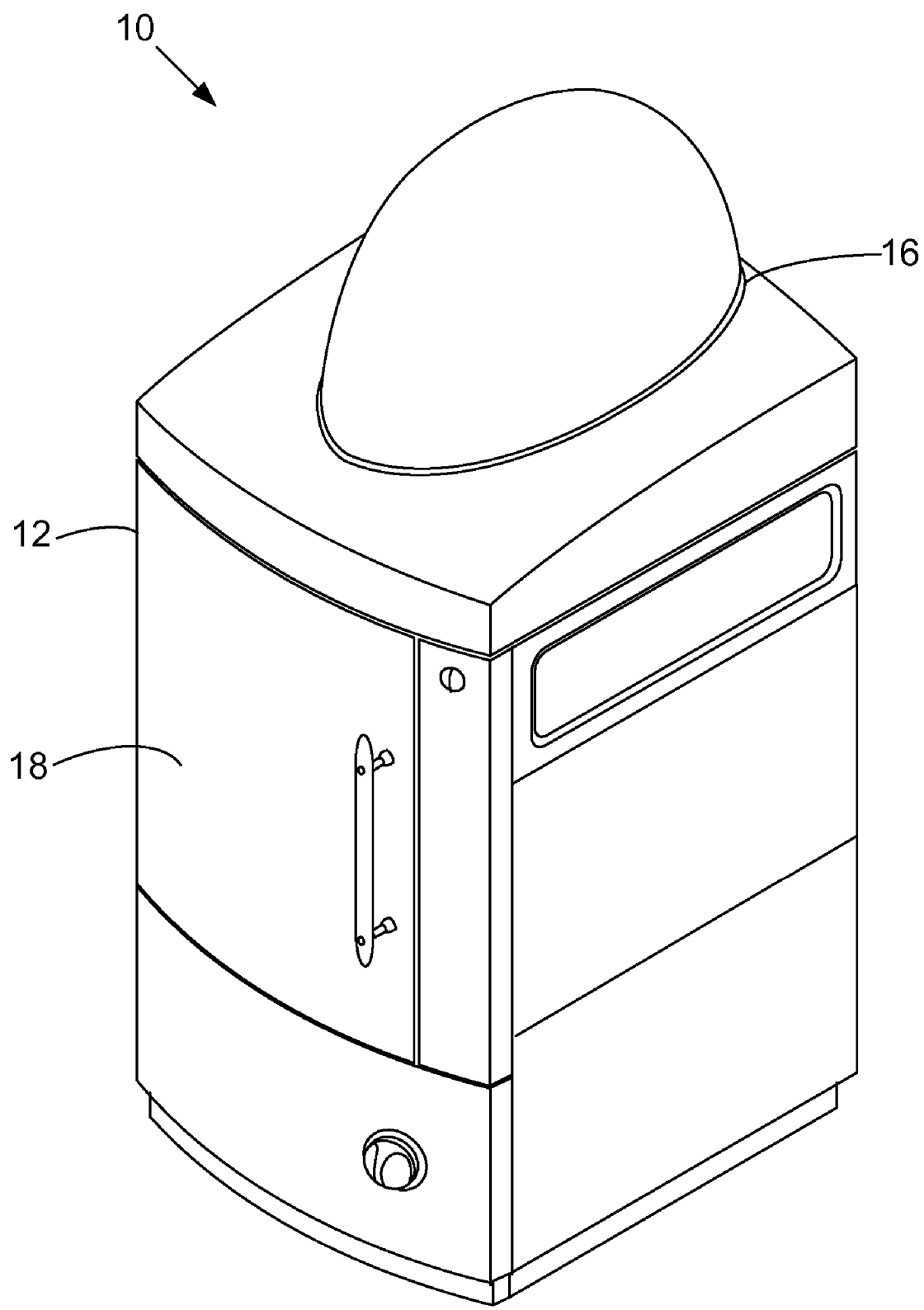
FIGS. 14A and 14B illustrate an imaging system configured to capture photographic, fluorescent and structured light images of a mouse in accordance with one embodiment of the present invention.
Figure 14B:
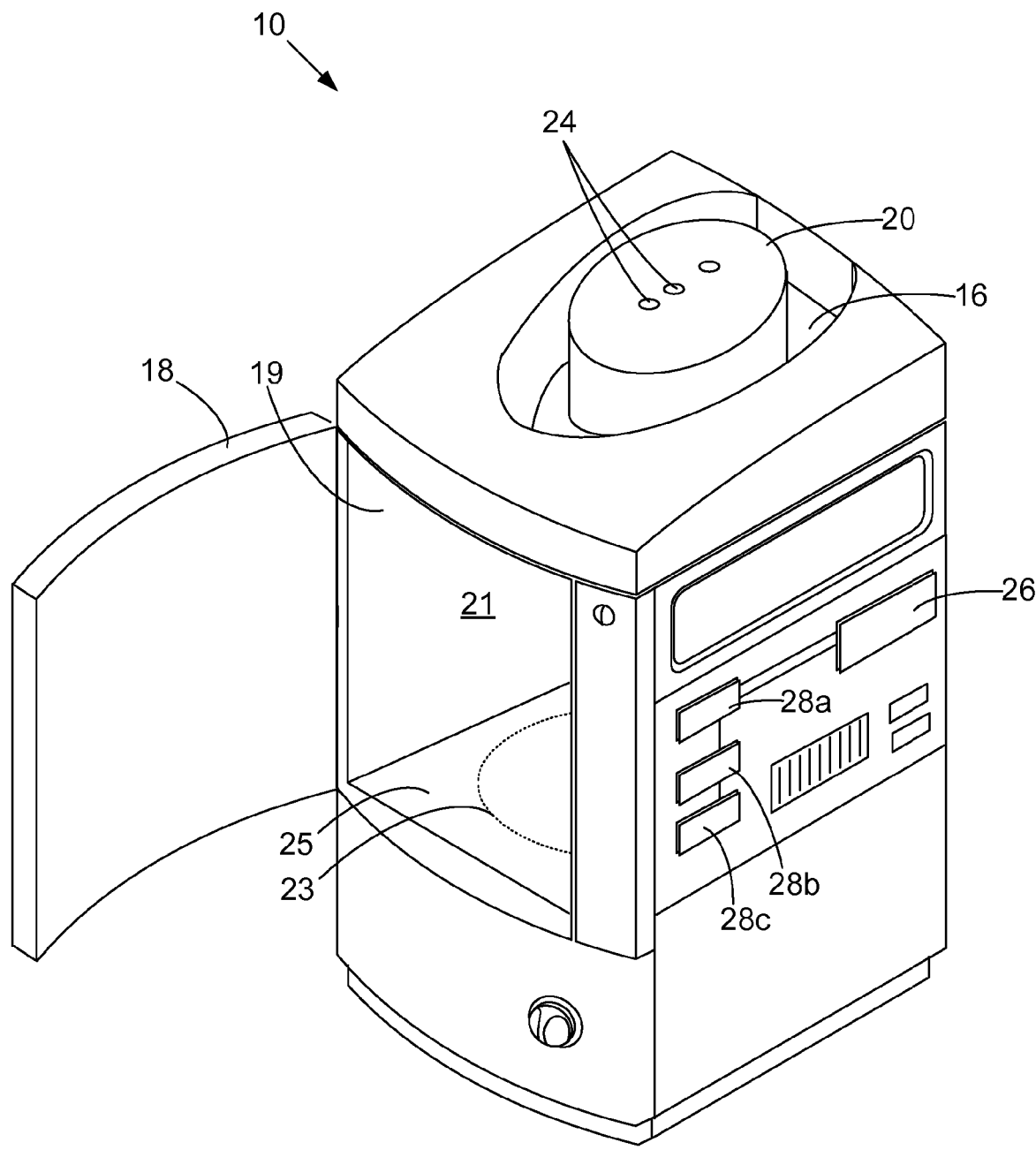

Image capture 202 uses box 10 of FIGS. 14A and 14B. In this case, image capture 202 begins be receiving a mouse in an imaging box (220). This often occurs when a user places the mouse on a stage within an imaging chamber for the imaging box. The user may also initiate image capture 202 using a computer associated with the imaging system.

In one embodiment, the stage is movable. In this case, the imaging system moves the stage to a desired position according to a control signal provided by a computer in the imaging system (222). For example, a user may input a desired image position via the computer user interface, and the imaging control system moves the stage accordingly. Alternatively, a desired position for the stage may be pre-programmed based on an automated data collection routine that the user initiates. A moving stage allows multiple positions and angles relative to a fixed camera.

The camera then captures a structured light image (224). Structured light image capture may be accomplished using a structured light projection system. In a specific embodiment, the structured light projection system projects structured light down onto the mouse from an angle, and the camera (also above the mouse, or on the same side of the mouse as the projector) captures the altered structured light. Suitable structured light generation systems are described in commonly owned and co-pending patent application Ser. No. 11/127,842. The structured light image data is also transferred to an image processing unit and/or a processor in the imaging system for storage for further processing to build a 3D surface representation.

A camera then captures a photographic image (226). The photographic image data is transferred to an image processing unit and/or a processor in the imaging system for storage. The photographic image may be subsequently used for display. For example, the photographic image may be used in an overlay image that includes both the photographic image and fluorescent probe distribution (output from 210). The overlay provides a simple pictorial view to facilitate user visualization of the internal fluorescent probe distribution.

The camera then captures a fluorescent light image (228). Fluorescence imaging illuminates the mouse to excite fluorescence molecules in the internal fluorescent probe, and then captures an image of the mouse, or a portion thereof, as the internal probe fluoresces. Fluorescent image capture provides incident light onto into the mouse with an illumination source. The incident light should be large enough in magnitude to elicit a fluorescent from the probe, but not too large so as to saturate a CCD camera. In response to the incident light, light emits from the "excited" fluorescent probe.

Figure 6A:
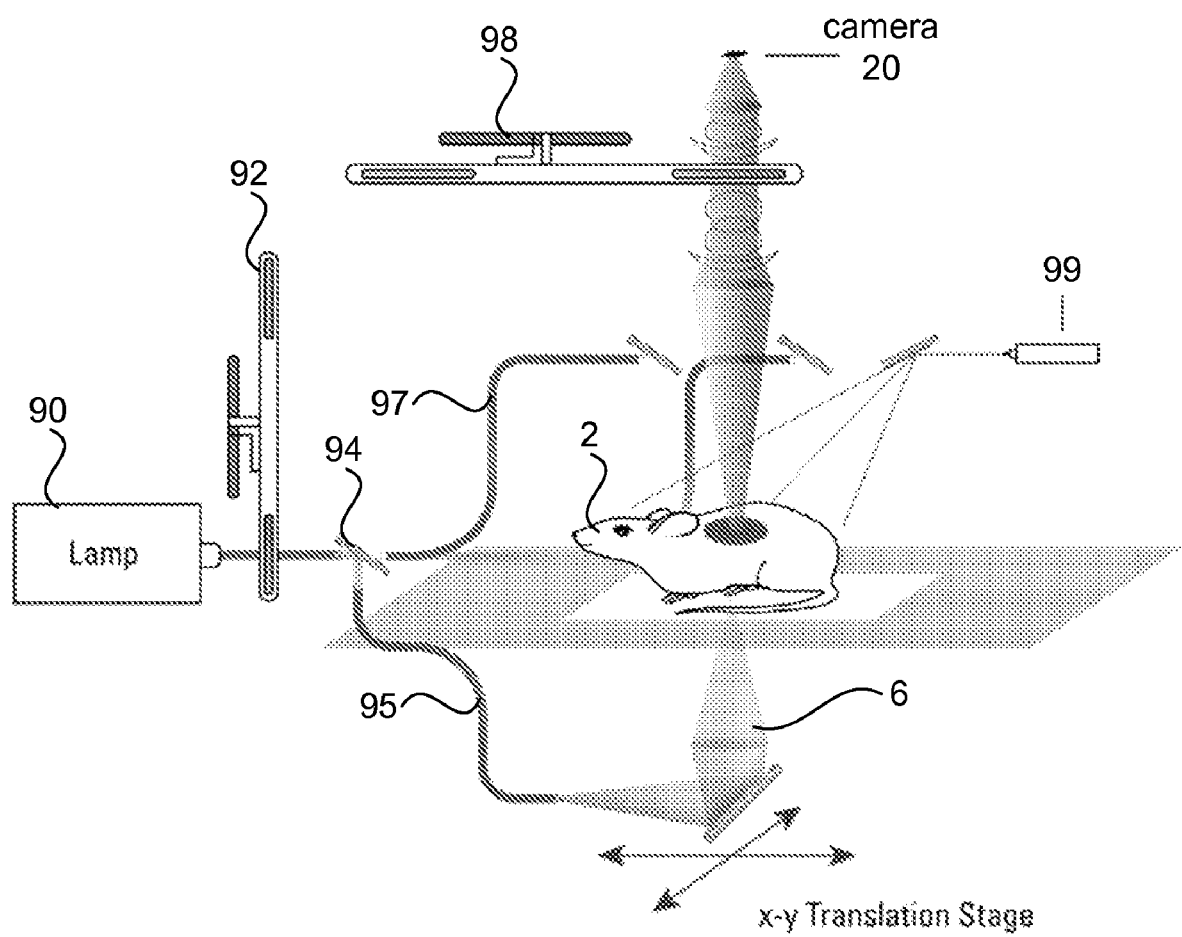
FIG. 6A schematically shows trans-illumination in accordance with one embodiment.

Trans-illumination and/or epi-illumination may be used. FIG. 6A schematically shows trans-illumination in accordance with one embodiment. Trans-illumination provides light from a side of the mouse opposite to the camera (e.g., incident light from below and a camera above), so that the light travels through the mouse. This provides lower levels of autofluorescence, which is useful for 3D tomographic reconstructions. Also, the ability to move the transillumination point relative to a fluorescent probe fixed within the animal, provide additional information that is use for 3D tomographic reconstructions. In this case, the excitation light source 4 includes a lamp 90 that provides light that passes through a filter in excitation filter wheel 92, which allows a user to change the spectrum of the incident excitation light. A fiber bundle switch 94 directs the excitation light into one of two paths 95 and 97. Path 95 is used for trans-illumination and directs the incident light along a fiber bundle or cable for provision towards a bottom surface of the mouse 2. In one embodiment, the outlet position of path 95 can be moved or re-directed to create multiple incident excitation light locations of trans-illumination path 95.

Figure 6B:
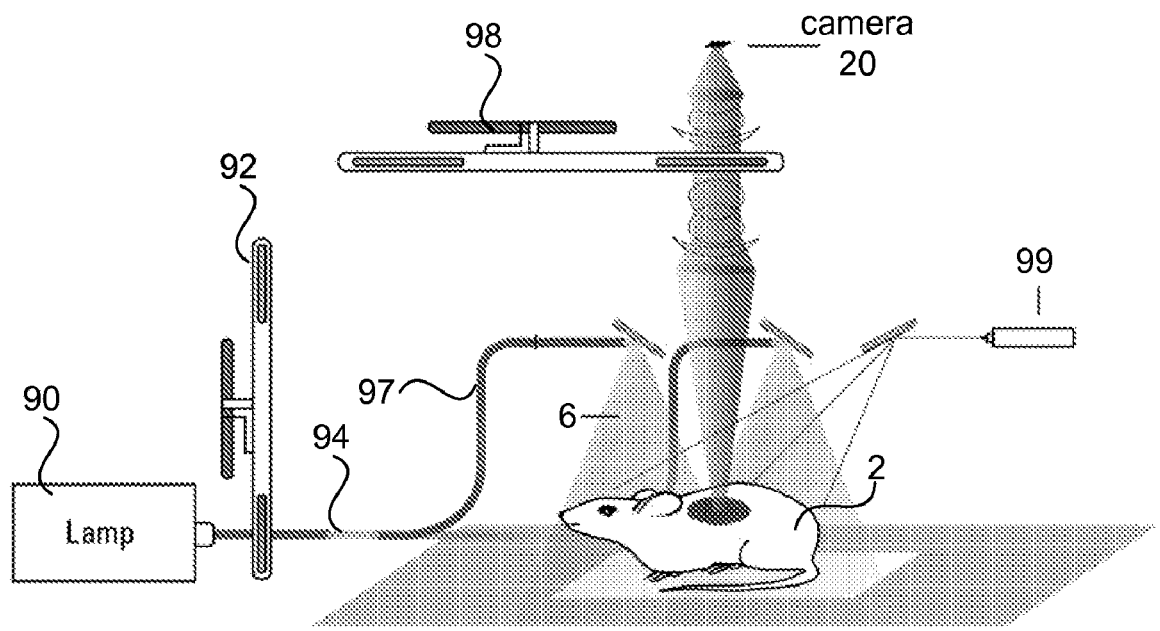
FIG. 6B schematically shows epi-illumination in accordance with one embodiment.

Epi-illumination provides the incident light from the same side of the animal that an image is captured (e.g., incident light from above, and a camera above the mouse), and is often referred to as reflection-based fluorescent imaging. FIG. 6B schematically shows epi-illumination in accordance with one embodiment. In this case, switch 94 directs the excitation light into path 97, where it routs to a position above the mouse for provision towards a top surface of the mouse 2 on the same side of the mouse as camera 20.

Epi-illumination provides a faster survey of the entire animal, but may be subject to higher levels of autofluorescence. Both trans-illumination and epi-illumination may be used. Epi-illumination avoids significant light attenuation through the mouse, and may help constrain volume elements near the camera-facing surface of the mouse. For example, the epi-illumination constraints may identify artifact voxels near the top surface, which are then removed by software.

In either case, an emission filter 98 allows a user to control a spectrum of light received by camera 20. This combination of excitation filter wheel 92 and emission filter 98 allows images to be captured with numerous combinations of excitation and emission wavelengths. In a specific embodiment, excitation filter wheel 92 includes twelve filters while emission filter 98 includes 24 positions.

Imaging may also capture both trans- and epi-illumination images, and combine the data. In each view, the light takes a different path through mouse, which provides a different set of input criteria and internal light conditions for tomographic reconstruction calculations.

A structured light source 99 also provides structured light onto the top of the animal for structured light image capture by the camera 20 without moving the mouse 2 on the horizontal surface.

In another embodiment, the stage is moveable, which allows camera 20 to capture images from multiple perspectives relative to the mouse 2. The stage may move in one dimension (e.g., up and down or side to side) or two dimensions for example.

In one embodiment, the fluorescent excitation uses a different spectrum than the fluorescent emission. As one of skill in the art will appreciate, the bandgap between excitation and emission filters will vary with the imaging system used to capture the images. A bandgap of at least 25 nm is suitable for many imaging systems. The excitation spectrum may be achieved using any combination of lights and/or filters. The emission spectrum will depend on a number of factors such as the fluorophore used, tissue properties, whether an emission filter is used before the camera, etc. In one embodiment, the transillumination location of the excitation light source is moved to capture multiple images of internal fluorescence and the same set of excitation and emission filters is used for the different excitation light source positions.

A camera then captures a fluorescent light image of at least a portion of the mouse (228). The fluorescent image records fluorescence as a function of 2D position. The image may include the entire mouse, or a portion of interest that has been zoomed in on (optically or digitally). The image is transferred to the image processing unit and/or computer for subsequent processing.

Figure 7:
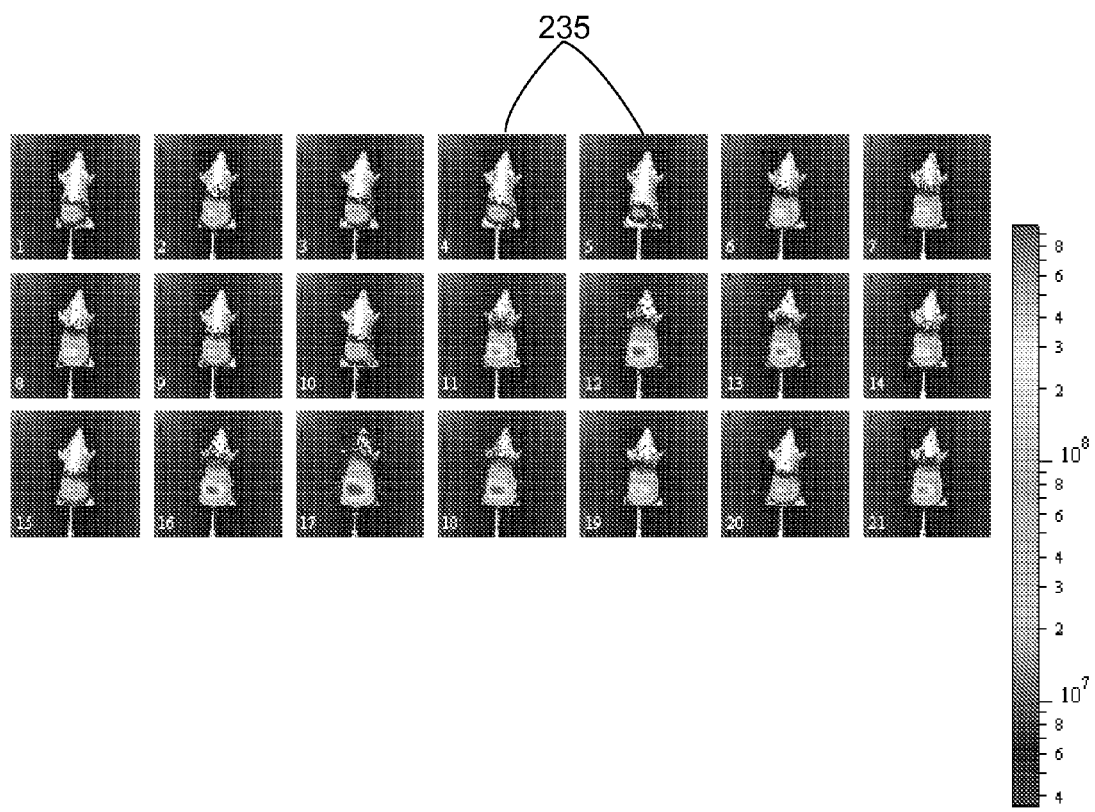
FIG. 7 illustrates sample images, each taken with a different trans-illumination position of an excitation light source.

Multiple fluorescent light images may be captured with the mouse in its current position (230). In one embodiment, this is done to facilitate spectral unmixing, where each image capture (228) uses a different excitation and/or emission spectrum. In another embodiment, multiple images are taken for differing trans-illumination positions of the excitation light source 4 (FIG. 1). Each trans-illumination position provides a different set of input conditions to the tomographic reconstruction. FIG. 7 illustrates 21 sample images 235, each taken with a different trans-illumination position of the excitation light source. In this case, the imaging system is configured to move the excitation light source (or has multiple excitation light sources that are controllably turned on/off) and captures an image of the mouse for each different trans-illumination position of the excitation light source.

All of the images 235 may be used in a tomographic reconstruction, or a subset can be used. The subset may be selected based on a quality measure for the images, such as a threshold for number of fluorescent photons collected in each image. Other quality measures may be used to select the images. The number of images captured may vary. In one embodiment, 1 to about 80 different trans-illumination positions and images are suitable for tomographic reconstruction. In a specific embodiment, from about 4 to about 50 images are suitable. The images may be stored for tomographic assessment at a later time, e.g., the images—or a subset thereof—are recalled from memory during tomographic processing.

In one embodiment, the stage and mouse may then be moved to a second position (232). While the stage is at the second position, one or more photographic, structured light, and/or fluorescent images of the mouse may be captured (224-230). Image collection may further continue by capturing images of the sample from additional positions and views. For example, image capture may occur at anywhere from 2 to 200 positions of the mouse within an imaging chamber. In general, as more images are captured, more information is gathered for tomographic reconstruction. Also, multiple structured light positions may be used to images more of the mouse in 3D. Eight positions, spaced every 45 degrees about a nose-to-tail axis of the mouse, is suitable in some 3D embodiments to build a stitched together surface representation for 360 degree viewing about the mouse.

In one embodiment, image capture 202 is automated. A user may initiate software included with an imaging system that controls components of the imaging system responsible for image capture. For example, the user may launch imaging and acquisition software on a computer associated with the imaging system that initializes the camera and carries out imaging automatically. According to stored instructions, the software may then select a desired stage position if a moveable stage is used, prepare the system for photographic, structured light, and/or fluorescent image capture (e.g., turn on/off lights in the box), focus a lens, selectively position an appropriate excitation or emission filter, select an excitation fluorescent light source (one of many for example), set an f-stop, transfer and store the image data, build a reconstruction, etc. For fluorescent image capture, software activates the camera to detect photons emitted from the mouse, which usually corresponds to absolute units from the surface. The camera may capture the fluorescent image quickly or over an extended period of time (up to several minutes).

Additional processing may occur on the fluorescent images. Fluorescent imaging often captures image data with multiple reporters; each reporter may have its own wavelength spectrum. A camera image of a mouse with multiple reporters has the spectral results of each reporter mixed together. In this case, spectral unmixing is useful to clean fluorescent image data and separate the contributions from each source before tomographic processing. The unmixing may also identify contributions from autofluorescence. In one embodiment, a spectral unmixing tool is employed in software to separate fluorescent contributions from multiple sources. This permits fluorescent tomography described herein to image multiple reporters in a mouse independently. For example, one reporter may be used in an imaging application to monitor cell death in the mouse, while the second reporter monitors cell propagation. A user may initiate the spectral unmixing tool and software with an appropriate user interface command.

Figure 9:
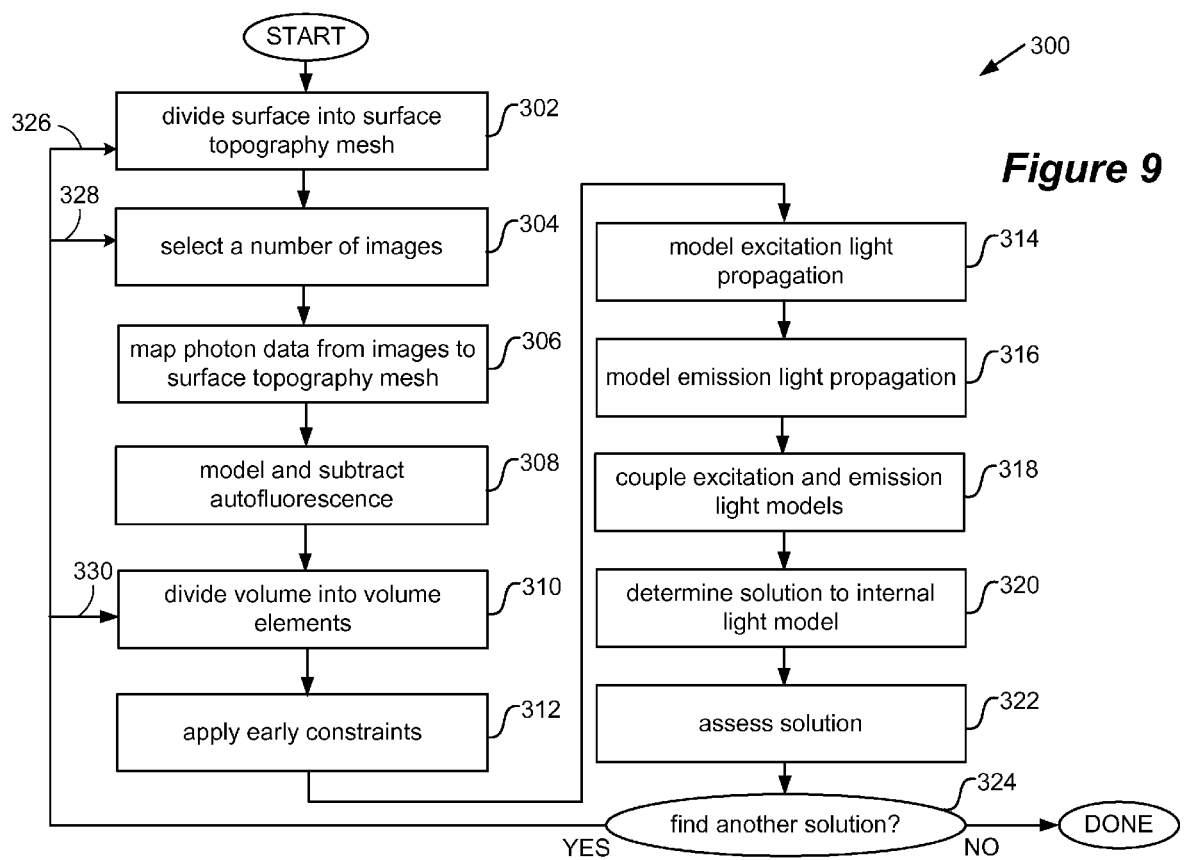
FIG. 9 shows a process flow for obtaining a three-dimensional representation of a fluorescent probe distribution located inside mouse in accordance with a specific embodiment of the present invention.

FIG. 9 shows a process flow 300 for obtaining a 3D representation of a fluorescent probe distribution located inside mouse 2 in accordance with a specific embodiment of the present invention. Process flow 300 expands upon method 200 of FIG. 2, and converts surface light emission data to a mathematical representation of a fluorescent probe distribution within the mouse.

Process flow 300 first divides a surface representation for the mouse into a surface mesh that includes a set of surface elements (302). This may include obtaining a surface topography, if that has not already been done (see 204 in FIG. 2). The number of surface elements will vary according to the mouse surface area and a desired solution accuracy for the tomographic reconstruction. The number of surface elements in the set should be large enough to capture photon density details and variation across the mouse surface. For example, between about 100 and about 10,000 surface elements may be suitable for a mouse.

Process flow 300 then selects a number of images for use in the tomographic assessment (304). As mentioned above in image capture, not all images previously captured and stored in memory need be used. For example, a user may select images that include a moving trans-illumination light source that is closer to a fluorescent probe compared to other images where the moving trans-illumination light source is farther away from the probe. Epi-illumination images may also be incorporated into process flow 300.

Process flow 300 maps photon data from the images to the surface topography mesh (306). This may use the mapping techniques described above in 206 of FIG. 2.

Expanding upon the mapping described above with respect to 206 in FIG. 2, the mapping converts surface light data (excitation and/or emission) into light data internal to a surface. Notably, this relates surface emission intensity to photon density just inside the mouse surface. In one embodiment, process flow 300 converts values of light emission intensity for each surface element into photon density just inside the surface. Referring briefly to FIG. 5, the value of emission intensity at a surface element, $I(\theta_2)$, is related to the photon density $\rho$ beneath the surface element. The exact form of the relationship depends on the model used to describe the transport of photons across the surface boundary. One embodiment of this relationship, based on the partial-current boundary condition, is given by:

$$I(\theta_2) = \frac{c}{4\pi n^2} T(\theta)\cos\theta_2 d\Omega \left[1 + \frac{3}{2}\frac{1-R_{eff}}{1+R_{eff}}\cos\theta\right]\rho \quad (1)$$

Here, c is the speed of light, n is the index of refraction of the sample medium, T is the transmission coefficient for light exiting the sample through the surface element, and $\theta$ is the internal emission angle, which is related to the external emission angle $\theta_2$ through Snell's law:

$$n \sin\theta = \sin\theta_2 \quad (2)$$

The parameter $R_{eff}$ is the average internal reflection coefficient calculated from the following formulae:

$$R_{eff} = \frac{R_\phi + R_j}{2 - R_\phi + R_j} \quad (3)$$

$$R_\phi = \int_0^{\frac{\pi}{2}} 2\sin\theta\cos\theta R(\theta) d\theta$$

$$R_j = \int_0^{\frac{\pi}{2}} 3\sin\theta\cos^2\theta R(\theta) d\theta$$

$$R(\theta) = \begin{cases} \frac{1}{2}\left(\frac{n\cos\theta_2 - \cos\theta}{n\cos\theta_2 + \cos\theta}\right)^2 + \frac{1}{2}\left(\frac{n\cos\theta - \cos\theta_2}{n\cos\theta + \cos\theta_2}\right)^2 & \text{for } \theta < \arcsin(1/n) \\ 1 & \text{for } \theta > \arcsin(1/n) \end{cases}$$

Thus, the internal reflectivity $R_{eff}$ depends on the index of refraction of the medium underneath a surface element. In tissue for example, $R_{eff}$ is typically in the range of 0.3-0.5.

Eqs. (1) and (2) may thus be used to convert surface emission data measured at each surface element to values of the photon density beneath the surface.

Autofluorescence is then modeled and subtracted from the surface emission data (308). Suitable techniques for doing so were described above with respect to 208 in FIG. 2.

Figure 8:
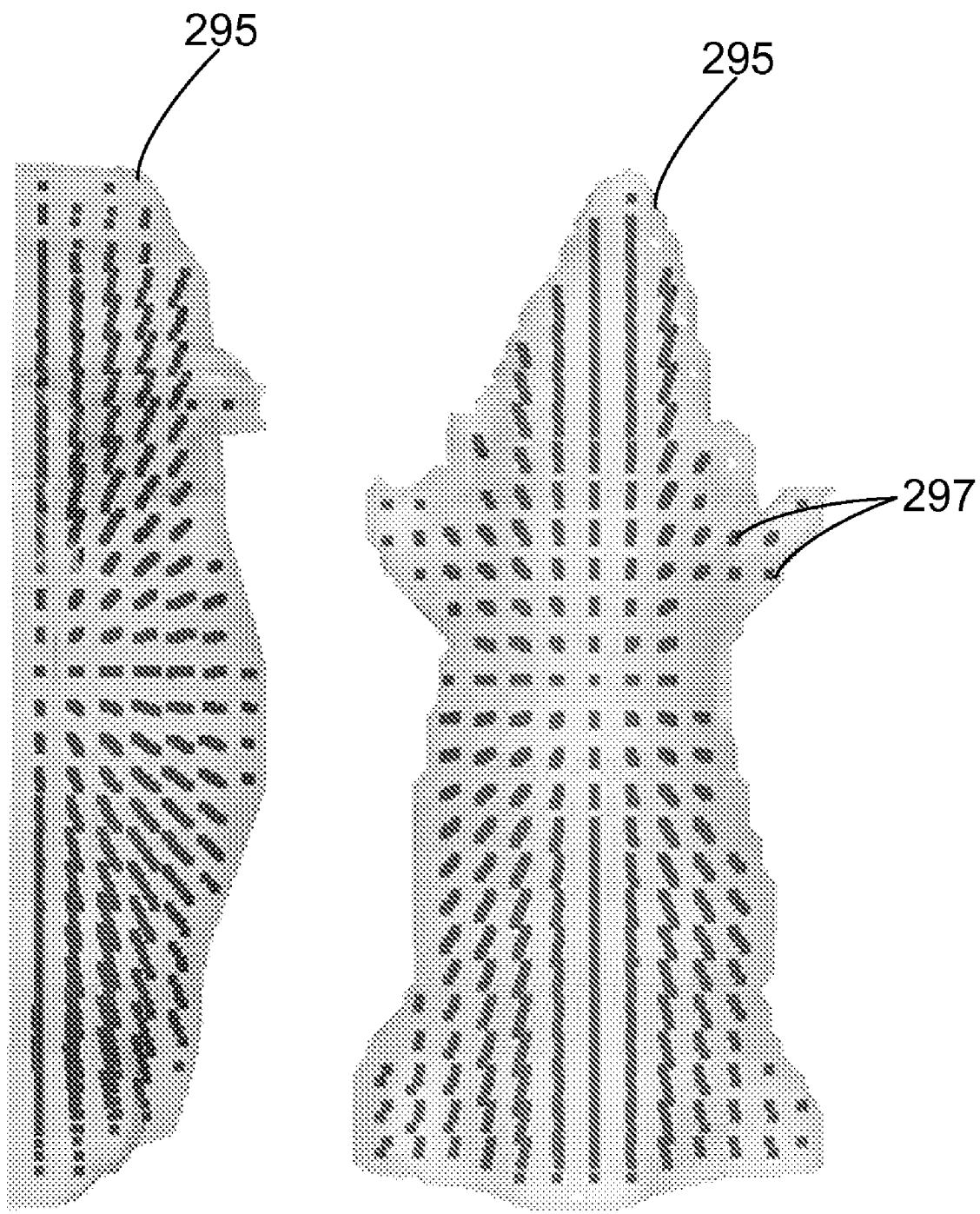
FIG. 8 shows sample side/lateral and top/dorsal view of a mouse representation that includes volume elements suitable for use in the method of FIG. 7.

Referring back to FIG. 9, process flow 300 then divides the mouse interior volume into volume elements, or 'voxels' (310). FIG. 8 shows sample side/lateral and top/dorsal view of a mouse 295 representation that includes volume elements 297. In one embodiment, each volume element 297 is considered to contain a point light source at its center. A solid mesh of volume elements 297 then defines a collection of point sources used to approximate light in the mouse. Volume elements 297 may also be used as a framework to describe the fluorescent probe distribution 5. In a specific embodiment, process flow 208 may use a volume element 297 resolution of about 0.5 to about 6 millimeters for a small mammal. A volume element 297 resolution of about 1 millimeter is suitable for some mice. Other volume element 297 sizes and densities may be used.

One or more early constraints may also be applied (312) to expedite or simplify the determination, such as applying one or more limits on the modeling and solution-space. In one embodiment, the internal light modeling solution space is spatially limited to within the boundaries of the mouse surface. In another embodiment, a volume space used within the reconstruction is limited by one or more practical considerations. For example, regions of the internal mouse volume far away from where fluorescent light emission takes place (e.g., the rear of the mouse when the head visibly shows the highest light emission density), as determined by a visual scan of the images, may be excluded from the solution space.

Process flow 300 then models light propagation. In the embodiment shown, this occurs in a three-step process where excitation light and emission light are each modeled separately and then the two are combined (314, 316, and 318).

Light transport in turbid media such as tissue is dominated by scattering and is essentially diffusive in nature. In one embodiment, tissue scattering and absorption parameters are known a priori, stored in memory, and recalled from memory when a reconstruction occurs. In another embodiment, tissue scattering and absorption parameters are calculated from trans-illumination measurements.

In many instances, the condition for diffusive transport is that the scattering coefficient $\mu_s$ be greater than the absorption coefficient $\mu_a$ so that the change in the photon density is small between scattering events. The photon density produced by a source power density, $U_i$, in a homogeneous medium may be represented by the diffusion equation:

$$D\nabla^2 \rho - \mu_a c \rho = -U_i(\underline{x}) \tag{4}$$

where the diffusion coefficient D is, $$D = \frac{c}{3(\mu_A + \mu_S)} \tag{5}$$

An emission Green's function is a solution to Eq. (9) subject to the boundary condition imposed by the surface of the sample.

In a specific embodiment, a Green's functions is used to model internal light propagation. A Green's function mathematically describes light propagation through space, such as through tissue, from one location to another. In one embodiment, the Green's function uses volume elements 297 and surface mesh elements as vector spaces for its data elements. In a specific embodiment, an excitation Green's matrix models light propagation from a position of the excitation illumination source to the volume elements 297 (314). An emission Green's matrix may also be used to model light propagation from the volume elements 297 to the surface elements (316).

The excitation and emission models are then combined (318). In a specific embodiment, the excitation and emission Green's function matrices are coupled together, along with a coupling constant, and form a single fluorescence Green's kernel matrix for the fluorescence forward model. In another specific embodiment, the excitation Green's function and emission Green's function matrices are composed using a hybrid Green's function expression which combines weighted terms of a radial partial current boundary condition and an extrapolated boundary condition. This coupled Green's function may be applied to fluorescence of the probe and/or autofluoresence.

Other modeling processing and factors are suitable for use. Modeling may also include one or more of: a) establishing a relationship between the surface elements and volume elements, b) setting additional limits on the modeling and solution-space, c) deciding whether to use a homogeneous or non-homogeneous model for light propagation in tissue, and/or d) composing a mathematical representation of light internal to the mouse. FIG. 10 describes modeling suitable for use with process flow 300 in more detail.

Referring back to FIG. 9, process flow 300 then determines the light data internal to the mouse, including the desired fluorescent probe distribution that includes the fluorescent probe (320). For example, once the Green's function is determined, the distribution is obtained by solving the system of linear equations that relate the photon density at the surface to the source distribution inside the object. In one embodiment, process flow 300 solves for all the internal volume elements. Thus, once the Green's function is modeled and determined, it may be evaluated for every volume element-surface element pair, in order to obtain the system of linear equations (Eq. 7, below). Referring forward to Eq. (7), since $\rho$ is known, and $G_{ij}$ can be determined as described below, the reconstruction method then solves the linear system, Eq. (7), for the source strengths $S_i$.

Typically, there is no exact solution to the linear system because the collection of point sources is only an approximation of the actual source distribution. One suitable reconstruction is then the best approximate solution of the linear system. In a specific embodiment, process flow 300 uses the non-negative least squares algorithm to solve for the internal fluorescent probe distribution. Other techniques may be used. In some cases where the fluorescent probe distribution includes a spatially smoother solution, Eq. (7) can be augmented using a regularizing matrix in the first derivative.

In one embodiment, the present invention relies on a simplified analytical approximation (planar boundary condition) for the Green's function as described above. In another embodiment, a look-up table can be used for the Green's function. The look-up table may be created by previous measurements of photon transport in a sample (or similar sample approximated to be substantially equal to the current sample), or by computational simulations using techniques such as Monte Carlo or finite element modeling. This particular method is useful for samples consisting of inhomogeneous media, such as animal subjects. In this case, the optical properties of the tissue, $\mu_a$ and $\mu_s$ may have spatial dependence or other heterogeneous properties.

FIG. 13A shows top and side views 380 and 382 of sample reconstructed results for a fluorescent probe distribution within a phantom mouse (e.g., plastic mouse having an embedded fluorescent probe). In this case, the reconstructed source 383 shows a fluorescent dye in the phantom mouse whose fluorescent yield values are above 10% of the maximum light value in the reconstructed solution. FIG. 13B shows reconstruction results for a fluorophore in a real mouse.

In one embodiment, process flow 300 applies an iterative solution process. Iterative processing obtains multiple three-dimensional representations and compares them to improve the final output and assessment for the fluorescent probe distribution. In this case, process flow 300 varies the tomographic assessment or modeling, finds a potentially new of different solution in each iteration, and then selects one of the multiple solutions. Loop 328, for example, varies the subset of images that were selected from a larger set of images.

To facilitate comparison between iterations, iterative process flow 210 assesses the solution quality and assigns a quality to each iterative solution (322). In one embodiment, the assessment measures a difference between the observed photon density and the calculated photon density. For example, a "chi squared" criteria may be used:

$$\chi^2 = \sum_i \left[ \frac{\rho_i - \sum_j G_{ij} s_j}{\rho_i} \right]^2 \tag{6}$$

The value of $\chi^2$ measures the difference between the observed photon density $\rho_i$ and the calculated photon density $$\sum_j G_{ij} s_j$$

over the surface of the sample. Other terms shows in Equation 6 are described further below with respect to Equations 7-9.

In one embodiment, iterative process flow varies volume element configuration. Loop 330 varies the number and/or size of volume elements. In this case, volume element size is initially set, and changed as iteration proceeds. In some cases, the initial voxelation is relatively coarse and refined with successive iterations. For example, the volume element size may be reduced by a factor of two in a next iteration. If the solution quality improves after this second pass, then the volume element size may be again reduced by a factor of two in a third iteration. If the solution quality doesn't improve or gets worse, then the algorithm may have converged on a final solution and stop. In one embodiment, the initial volume element size may range from about 0.1 mm$^3$ to about 1 cm$^3$, and subsequent and/or final volume element size for volume elements close to the source may reduce from about 1 mm$^3$ to about 10 mm$^3$. In a specific example, the initial volume element size may be about 200 mm$^3$ or about 1 cm$^3$, and the final volume element size for volume elements close to the source may reduce to about 1 mm$^3$.

In some cases, it is advantageous to reduce the number of volume elements in the problem while maintaining a high density of volume elements in the vicinity of the fluorescent probe. This can be achieved by using adaptive meshing. In one embodiment, adaptive meshing increases the density of the solid mesh near the probe to provide increased volumetric information in this space, while density of the solid mesh decreases in areas where no activity of interest is taking place (no light generation or transport). In one suitable adaptive meshing application, a coarse volume element mesh is initially applied throughout the entire sample volume and the current solution is found, yielding an initial solution for $S_j$. Next the volume elements that have source strengths greater than zero ($S_j$>0) are refined (i.e. subdivided) and those where the source strengths equal zero ($S_j$=0) are removed. Solution attainment and volume element mesh refinement may then be iterated repeatedly, producing a high-density volume element mesh localized around the fluorescent probe distribution. During each iteration, the quality of the current solution is assessed (322). In a specific embodiment, the iteration continues until further refinement produces no significant decrease in the assessment value.

An additional iterative improvement may be obtained by varying the number of surface elements, $N_s$, used in obtaining the three-dimensional representation (loop 326). Using a subset of the surface elements of the surface mesh reduces the number of constraints in the problem, which may simplify and expedite solution calculation. The number of surface elements may be used to sample the surface uniformly. In this case, process flow 300 iterates for different values of $N_s$ corresponding to sampling the surface element mesh at different densities, and use the quality assessment (322) to determine the best solution among the different values of $N_s$. For example, if the number of surface elements is between about 100 and about 300 surface elements for a small mouse, an iteration step size between about 10 and 50 may be suitable.

Figure 10:
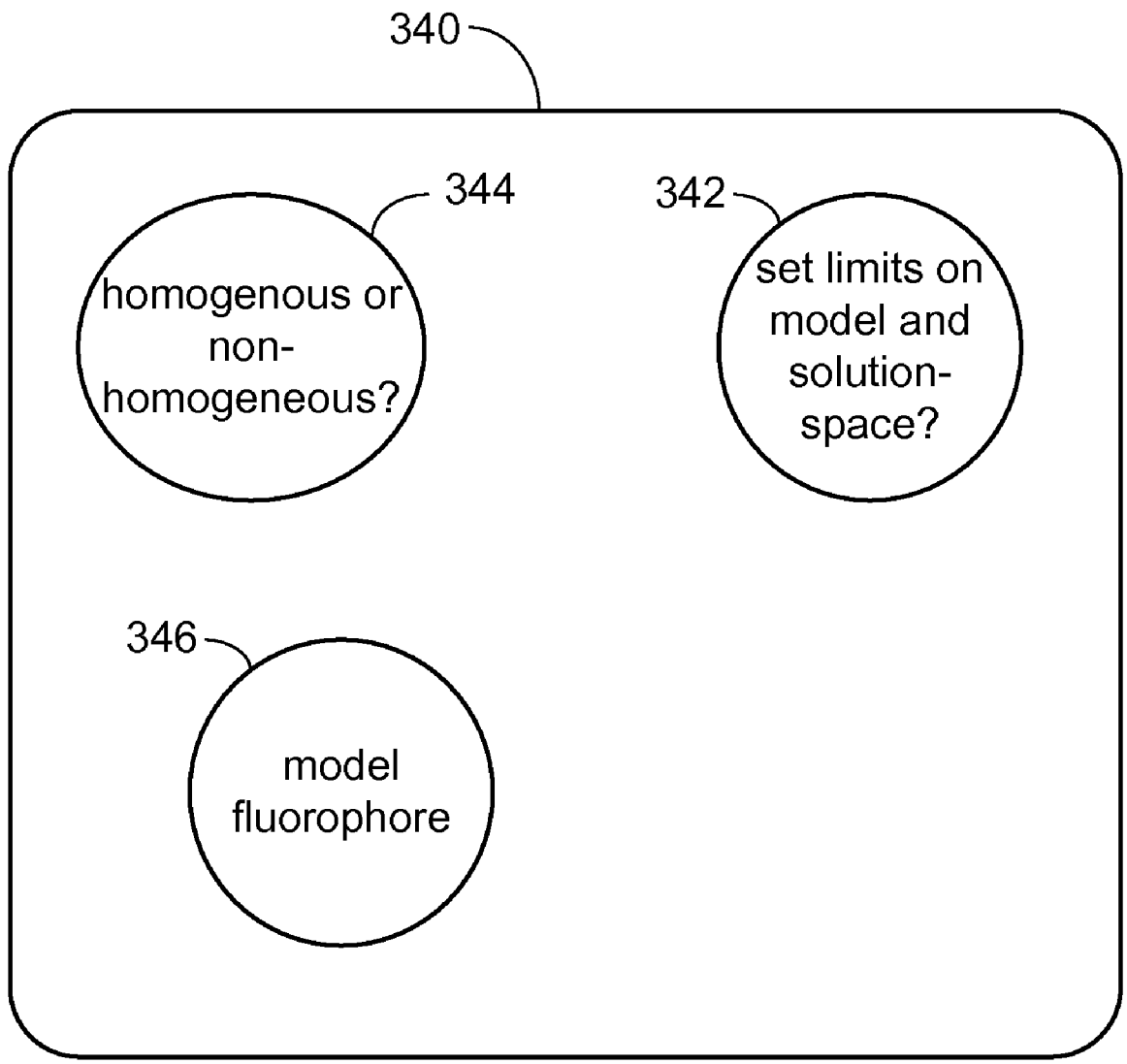
FIG. 10 expands upon a model used in the method of FIG. 9.

FIG. 10 expands modeling light propagation in a mouse in accordance with a specific embodiment of the present invention. Modeling 340 establishes a relationship between the surface elements and volume elements.

Figure 12:
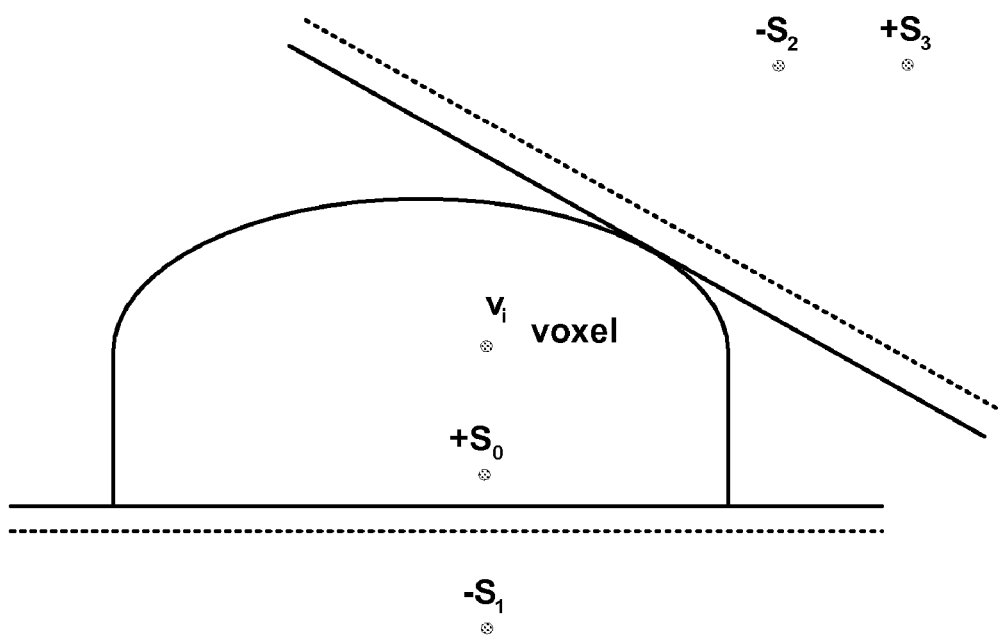
FIG. 12 illustrates a schematic diagram that models excitation light as it enters the mouse.

In one embodiment, the reconstruction uses a linear relationship between the source emission strength and the photon density at the surface. In a specific embodiment, the linear relationship is described by a Green's function. As mentioned before, the Green's function mathematically and numerically describes the transport of photons inside the mouse, and may accommodate for the effects of non-homogeneities in the volume and internal reflection at the boundary. In this case, the Green's function also describes the transport of photons inside the sample from each point or volume element in the distribution to the inside of each surface element. One useful form for the Green's function is a simplified approximation in which the surface of the sample is treated locally as a planar interface oriented tangent to a surface element, as shown in FIG. 12. The photon density at the surface is the analytical solution for a point source in a semi-infinite slab using the partial-current boundary condition. This allows the Green's function to be calculated with minimal computational expense. Other boundary conditions could be used.

Modeling 340 may incorporate additional information and constraints into the solution-space (342). Additional limits on a Green's function solution-space may apply the location of the input excitation signal at the surface. For example, if a trans-illumination fluorescent image is used, then the known (and potentially changing between images, see 230 in FIG. 3) bottom illumination source position may be included in the Green's function and modeling.

The model also selects or assigns homogeneous or non-homogeneous properties to the mammalian tissue (344). A mouse includes a turbid interior. A turbid interior refers to a volume that does not allow unimpeded transport of light. The turbid interior may comprise one or more mediums, structures, solids, liquids, gases, etc. In one embodiment, the sample is modeled as homogeneous such that each representative volume element in the sample is characterized by identical light transport properties. In another embodiment, the sample is represented as heterogeneous such that various representative volume elements in the sample are characterized by different light transport properties. In a mouse, the interior may comprise a mixture of tissues, bones, organs, etc., each of which may be characterized by separate light transport properties in a heterogeneous model. It is understood that animals are not fully homogeneous and that tissue absorption for living mammals varies with the type of tissue or tissue cells, and is generally affected by varying particles and quantities such as the presence of hemoglobin. However, software run by an imaging system may implement homogeneous or heterogeneous assumptions on the optical behavior of mammalian tissue when imaging a living mouse. Generally, Green's functions for homogeneous tissue models can be calculated analytically in real time for each imaging example, while more complex heterogeneous models require significant computational effort and may be saved in a look-up table.

Data for the fluorophore is then obtained 346, such as data related to its emission spectrum. In some embodiments, an emission spectrum for the fluorophore at one or more wavelengths is provided as an input to the model. The fluorophore(s) used in the fluorescent probe are typically known for an imaging application, and optical properties for the fluorophore wavelengths are also known and may be stored in software prior to imaging. In some cases, a user selects a wavelength filter, with its predetermined wavelength range, for image capture and the spectrum properties for the fluorophore at that wavelength range are input to the model. Alternately, the imaging process is automated and a computer recalls spectrum properties for the fluorophore from memory based on an automated wavelength filter selection. A graphical user interface associated with the imaging system may also allow a user to select one or more fluorophores from a list, where information for each fluorophore is stored in a database. Other fluorophore properties may include excitation spectrum and extinction coefficient and quantum efficiency, for example.

With a linear relationship between the source strength in each volume element and the photon density at each surface element described by a Green's function $G_{ij}$, the photon density at the ith surface element may be approximated by the sum of the contributions from all the volume elements:

$$\rho_i \cong \sum_j G_{ij} s_j \quad (7)$$

where $\rho_i$ represents photon density at the surface for the ith surface element. Generally, $\rho_i$ is known from the camera image data after it is mapped onto the surface, while $G_{ij}$ is known from the modeling, leaving $S_j$ to be solved for. In other words, $S_j$ refers to the amount of light in each volume element. For fluorescent tomographic reconstruction, $S_j$ includes two components: one from the fluorescent probe and a second from the autofluorescence, which may be represented as:

$$s_j = [S_{fluor} + S_{autofluor}]_j \quad (8)$$

For a fluorescent source, the relationship between the surface elements and the volume elements may accommodate both excitation and emission modeling. The Green's function in the linear system thus includes a) a first Green's function that describes the transport of the emission light from the volume elements to the sample surface and b) a second Green's function that describes the transport of the excitation light from the sample surface to the volume elements. In a specific approximation, the Green's function in the linear system (7) includes the product of two Green's functions: (need to fix eq 9)

$$G_{ij} = G_{ij}^{em} \sum_k G_{jk}^{ex} s_k^{ext} \quad (9)$$

The first Green's function, $G_i^E$, describes the transport of excitation light from the excitation source at the surface of the sample to the $i^{th}$ volume element. The second Green's function, $G_{ij}^F$, describes the transport of the fluorescent light from the $i^{th}$ volume element to the $j^{th}$ surface element. Both Green's functions can be determined from analytical expressions, such as the simplified approximation described above in the case of a homogeneous medium, or from look-up tables in the case of an inhomogeneous medium. The excitation and fluorescent light are typically at different wavelengths, and thus the fluorescence does not stimulate additional fluorescence.

Combining equations 7, 8, and 9, gives:

$$\rho_i \cong \sum_j \left[ G_{ij} s_j^{fluor} + G_{ij} s_j^{autofluor} \right] \quad (10)$$

If autofluorescence is modeled according to one of the methods described earlier with respect to FIG. 2, then the autofluorescence term in equation 10 can be subtracted from the measured photon density ($\rho_j$), resulting in the following equation to be solved for the fluorophore concentration $S_j^{fluor}$:

$$\rho_i - \sum_j G_{ij} s_j^{autofluor} \cong \sum_j G_{ij} s_j^{fluor} \quad (11)$$

As described previously, this equation can be solved by a non-negative least squares optimization method. Other methods for solving systems of linear equations can also be used.

Figure 11:
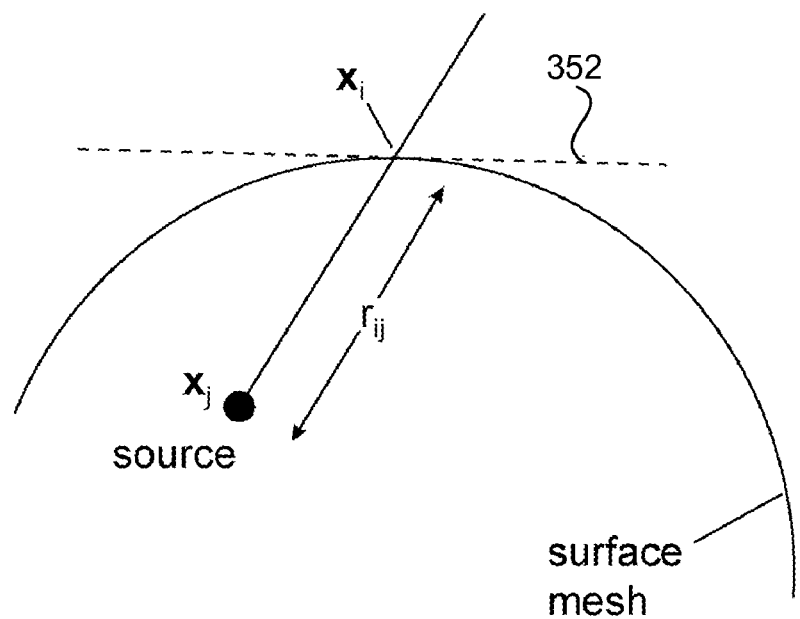
FIG. 11 illustrates a schematic diagram of a planar approximation for light emitting from a mouse.

In one embodiment, the reconstruction uses a tangential plane boundary approximation combined with a partial current boundary condition to model photon diffusion Green's function for each surface element. FIG. 11 illustrates a schematic diagram showing this emission planar approximation. A plane boundary 352 is drawn tangent to the ith surface element. The photon density in the planar approximation is the solution for the point source at $x_j$ in a semi-infinite slab defined by the plane boundary, subject to the partial current boundary condition. Specifically, the boundary condition is simplified to the case of a plane boundary, although the orientation of the boundary may change for each surface element.

This simplified emission Green's function is the analytical solution for a point source in the semi-infinite slab using the partial-current boundary condition:

$$G_{ij} = \frac{1}{2\pi D} \left\{ \frac{\exp(-\mu_{eff} r_{ij})}{r_{ij}} - \frac{1}{z_b} \exp(r_{ij}/z_b) E_1 \left[ \left( \mu_{eff} + \frac{1}{z_b} \right) r_{ij} \right] \right\} \quad (12)$$

Here $r_{ij} = |x_j - x_i|$, $E_1$ is the first order exponential integral and $$\mu_{eff} = \sqrt{3\mu_A(\mu_A + \mu_S')} \quad (13)$$

$$z_b = \frac{2D}{c} \frac{1 + R_{eff}}{1 - R_{eff}} \quad (14)$$

In the simplified model just described, the simplified Green's function depends only on the distance between the volume element and the surface, and the angle of the surface element. This method of calculating the Green's function is fast and can be performed in real time for each mouse surface. It is understood that it is not necessary to use this simplified approximation to define the Green's function.

A similar approximation solution for the excitation Green's function may be constructed. FIG. 12 illustrates a schematic diagram showing one suitable excitation approximation, which models light as it enters the mouse. In this case, four fictitious point sources, $S_0$-$S_3$, are used to model light onto a volume element. Sources $S_0$ and $S_1$ are considered with a partial-current boundary condition, while sources $S_2$ and $S_3$ are considered with an extrapolated boundary model. Again, the boundary condition for excitation is simplified to the case of a plane boundary, whose orientation may change for each surface element.

The planar boundary approximations discussed above work well for smooth surfaces with a large radius of curvature, and for cases where the absorption coefficient is not too small ($\mu_a > 0.1$ cm$^{-1}$). An advantage of the planar approximation technique described above is that it is computationally convenient for solving the diffusion equation with an arbitrary complex boundary such as a mouse. Areas with more structure, such as the head or the limbs of a mouse, may benefit from a more accurate model of the boundary. Using a finite element modeling code to calculate the Green's functions is one option to obtain a more accurate boundary model. Finite element codes such as Flex PDE, from PDE Solutions, Inc. may be used for example. Another option will be to extend the planar surface approximation to first order in curvature, which may allow continued use of analytic expressions for $G_{ij}$.

Although process flow 300 has been described with many simplifications to the model to expedite processing, fluorescent tomographic reconstruction is not limited by these simplified computational methods. For example, the Green's Function may be calculated without many of the simplifications described above, even at the cost of increased computational requirements. In addition, while process flow 300 describes a specific method of obtaining measurements of light emission from the mouse, process flow 300 is not limited to how the light emission data is obtained or to the use of any particular apparatus. For example, light emission data may be obtained from an independent source and stored as data within a computer, and not necessarily produced as the result of imaging via a complementary or local imaging system.

In addition, although the present invention has been described so far with respect to a fluorescent probe that emits light, process flow 300 may be used to obtain 3D reconstructions of any type of internal light source, including one or more bioluminescent sources.

The tomographic reconstruction techniques of the present invention are typically implemented by a suitable processor or computer-based apparatus. FIGS. 14A and 14B illustrate an imaging system 10 configured to capture photographic, fluorescent and structured light images of a mouse in accordance with one embodiment of the present invention. While tomographic reconstruction will now be described with respect to imaging system 10, it is understood that the tomographic reconstruction as described herein is well suited for use with other imaging systems.

Imaging system 10 may be used for imaging a low intensity fluorescent probe such as fluorescent molecules in a mouse and the like. The low intensity fluorescent probe may be included in any of a variety of living or non-living light-emitting samples. Non-living light-emitting samples may include calibration devices and phantom devices. Living light-emitting samples may include, for example, animals or plants containing light-emitting molecules, tissue culture plates containing living organisms, and multi-well plates (including 96, 384 and 864 well plates) containing living organisms. Animals may include any mammal, such as a mouse or rat containing luciferase-expressing cells.

System 10 finds wide use in imaging and research. The ability to track light-emitting cells in a small laboratory animal such as a mouse or rat opens up a wide range of applications in pharmaceutical and toxicological research. These include in vivo monitoring of infectious diseases, tumor growth in metastases, transgene expression, compound toxicity, and viral infection or delivery systems for gene therapy. The ability to detect signals in real-time and in living animals means that the progression of a disease or biological process can be studied throughout an experiment with the same set of animals without a need to sacrifice for each data point.

Imaging system 10 comprises an imaging box 12 having a door 18 and inner walls 19 (FIG. 14B) that define an interior cavity 21 that is adapted to receive a mouse 2 in which low intensity light is to be detected. Imaging box 12 is suitable for imaging including the capture of low intensity light on the order of individual photons, for example. Imaging box 12 is often referred to as "light-tight". That is, box 12 seals out essentially all of the external light from the ambient room from entering the box 12, and may include one or more seals that prevent light passage into the box when door 18 is closed. In a specific embodiment, door 18 comprises one or more light-tight features such as a double baffle seal, while the remainder of chamber 21 is configured to minimize any penetration of light into cavity 21.

Mouse 2 is placed within box 12 for imaging by opening door 18, inserting the mouse in chamber 21, and closing door 18. Suitable imaging systems are available from Xenogen Corporation from Alameda, Calif., and include the IVIS® Spectrum, IVIS® 3D Series, IVIS® 200 Series, IVIS® 100 Series, and IVIS® Lumina. Further description of a suitable imaging box 12 is provided in commonly owned U.S. Pat. No. 7,113,217 entitled "3-D Imaging Apparatus for In-Vivo Representations", which is incorporated by reference herein in its entirety for all purposes. Although imaging system 10 is shown with a single cabinet design, other embodiments of the present invention include a disparate imaging box 12 and desktop computer that includes processing system 28 and a dedicated display.

Imaging box 12 includes an upper housing 16 adapted to receive a camera 20 (FIG. 14B). A high sensitivity camera 20, e.g., an intensified or a charge-coupled device (CCD) camera, is mounted on top of upper housing 16 and positioned above imaging box 12. CCD camera 20 is capable of capturing luminescent, fluorescent, structured light and photographic (i.e., reflection based images) images of a living sample or phantom device placed within imaging box 12. One suitable camera includes a Spectral Instruments 620 Series as provided by Spectral Instruments of Tucson, Ariz. CCD camera 20 is cooled by a suitable source thermoelectric chiller. Other methods, such as liquid nitrogen, may be used to cool camera 20. Camera may also be side-mounted, or attached to a moving chassis that moves the camera in cavity 21.

Imaging system 10 may also comprise a lens (not shown) that collects light from the specimen or phantom device and provides the light to the camera 20. A stage 25 forms the bottom floor of imaging chamber 21 and includes motors and controls that allow stage 25 to move up and down to vary the field of view 23 for camera 20. A multiple position filter wheel may also be provided to enable spectral imaging capability. Imaging box 12 may also include one or more light emitting diodes on the top portion of chamber 21 to illuminate a sample during photographic image capture. Other features may include a gas anesthesia system to keep the mouse anesthetized and/or a heated shelf to maintain an animal's body temperature during image capture and anesthesia.

Imaging box 12 also includes one or more fluorescent excitation light sources. In one embodiment, box 12 includes a trans-illumination device and an epi-illumination device. As mentioned above with respect to FIGS. 6A and 6B, the trans-illumination device is configured to direct light into a first surface of the mouse, where diffused light exits a second surface of the mouse. The epi-illumination device is configured direct light onto a third surface of the specimen, where the diffused light exits the third surface of the mouse. Further description of fluorescent excitation light sources is provided in commonly owned and co-pending patent application Ser. No. 11/434,606, which is incorporated by reference in its entirety for all purposes.

A structured light source is included in imaging box. The structured light source includes a mechanism for transmitting a set of lines onto the object from an angle. The lines are displaced, or phase shifted relative to a stage, when they encounter an object with finite height, such as a mouse. This phase shift provides structured light information for the object. Camera 20 then captures the structured light information. Using software that employs a structured light analysis, surface topography data for the object (over its entire surface or a portion) is determined from the phase shift of the lines.

FIG. 14B shows system 10 with the removal of a side panel for imaging box 12 to illustrate various electronics and processing components included in system 10. Imaging system 10 comprises image processing unit 26 and processing system 28. Image processing unit 26 optionally interfaces between camera 20 and processing system 28 and may assist with image data collection and video data processing. Processing system 28, which may be of any suitable type, comprises hardware including a processor 28a and one or more memory components such as random-access memory (RAM) 28b and read-only memory (ROM) 28c.

Processor 28a (also referred to as a central processing unit, or CPU) couples to storage devices including memory 28b and 28c. ROM 28c serves to transfer data and instructions uni-directionally to the CPU, while RAM 28b typically transfers data and instructions in a bi-directional manner. A fixed disk is also coupled bi-directionally to processor 28a; it provides additional data storage capacity and may also include any of the computer-readable media described below. The fixed disk may be used to store software, programs, imaging data and the like and is typically a secondary storage medium (such as a hard disk).

Processor 28a communicates with various components in imaging box 12. To provide communication with, and control of, one or more system 10 components, processing system 28 employs software stored in memory 28c that is configured to permit communication with and/or control of components in imaging box 12. For example, processing system 28 may include hardware and software configured to control camera 20. The processing hardware and software may include an I/O card, control logic for controlling camera 20. Components controlled by computer 28 may also include motors responsible for camera 20 focus, motors responsible for position control of a platform supporting the sample, a motor responsible for position control of a filter lens, f-stop, etc.

Processing system 28 may also interface with an external visual display (such as computer monitor) and input devices such as a keyboard and mouse. A graphical user interface that facilitates user interaction with imaging system 10 may also be stored on system 28, output on the visual display and receive user input from the keyboard and mouse. The graphical user interface allows a user to view imaging results and also acts an interface to control the imaging system 10. One suitable imaging software includes "LivingImage" as provided by Xenogen Corporation of Alameda, Calif.

Processing system 28 may comprise software, hardware or a combination thereof. System 28 may also include additional imaging hardware and software, tomographic reconstruction software that implements process flows and methods described above, and image processing logic and instructions for processing information obtained by camera 20. For example, stored instructions run by processor 28a may include instructions for i) receiving image data corresponding to light emitted from a mouse as described herein, ii) building a 3-D digital representation of a fluorescent probe internal to a mouse using data included in an image, and iii) outputting results of the tomographic reconstruction on a display such as a video monitor.

Imaging system 10 employs a quantitative model that estimates the diffusion of photons in tissue. In one embodiment, the model processes in vivo image data and in order to spatially resolve a 3D representation of the size, shape, and location of the light emitting source. Regardless of the imaging and computing system configuration, imaging apparatus 10 may employ one or more memories or memory modules configured to store program instructions for obtaining a 3D representation of a probe located inside a sample and other functions of the present invention described herein. Such memory or memories may also be configured to store data structures, imaging data, or other specific non-program information described herein. Because such information and program instructions may be employed to implement the systems/methods described herein, the present invention relates to machine-readable media that include program instructions, state information, etc. for performing various operations described herein. Examples of tangible machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter. The invention may also be embodied in a carrier wave traveling over an appropriate medium such as airwaves, optical lines, electric lines, etc.

While this invention has been described in terms of several preferred embodiments, there are alterations, permutations, and equivalents which fall within the scope of this invention which have been omitted for brevity's sake. For example, although the methods have primarily been discussed with respect to fluorescent light imaging, the present invention is also well-suited for use with other wavelength ranges and imaging modalities, such as near IR. In addition, although the methods have been described with respect to solving for autofluorescence separately from the tomographic reconstruction to expedite finding a solution, they may be combined to accommodate minor changes in tissue properties, albeit with less constrained computations and a need for more computational resources. It is therefore intended that the scope of the invention should be determined with reference to the appended claims.

What is claimed is:

1. A method for obtaining a light distribution located inside an animal, the method comprising:

obtaining one or more fluorescent images of at least a portion of the animal;

obtaining a three dimensional representation of a surface portion of the animal;

dividing the three dimensional surface representation into a set of surface elements;

mapping fluorescent image data from the one or more fluorescent images to the set of surface elements to create fluorescent light emission data from the set of surface elements;

creating a set of volume elements within the animal;

converting the fluorescent light emission data from the set of surface elements into photon density internal to the animal using the set of surface elements and the set of volume elements; and determining a three-dimensional representation of a fluorescent probe distribution internal to the animal with a processor using the photon density internal to the animal and the set of volume elements.

2. The method of claim 1 wherein obtaining the one or more fluorescent images includes capturing an image of the animal with a camera while the animal rests on a horizontal surface.

3. The method of claim 2 further comprising providing fluorescent excitation light onto the animal.

4. The method of claim 3 wherein the fluorescent excitation light is incident in an epi-illumination mode or a trans-illumination mode.

5. The method of claim 1 wherein a first fluorescent image includes a first position for an excitation light source and a second fluorescent image includes a second position for the excitation light source.

6. The method of claim 5 wherein the first position for the excitation light source includes a first trans-illumination position and the second position for the excitation light source includes a second trans-illumination position.

7. The method of claim 6 wherein a camera that captures the images does not move between image capture of the first fluorescent image and image capture of the second fluorescent image.

8. The method of claim 7 wherein the first fluorescent image is captured from one camera perspective relative to the animal and the second fluorescent image is captured from a second camera perspective relative to the animal.

9. The method of claim 5 wherein the first fluorescent image is captured at a first combination of excitation and emission wavelengths and the second fluorescent image is captured at a second combination of excitation and emission wavelengths.

10. The method of claim 1 further comprising:
dividing the surface portion into a set of surface elements;
dividing an interior of the animal into a set of volume elements; and
establishing a relationship between the set of surface elements and the set of volume elements.

11. The method of claim 1 wherein tissue in the animal is modeled as homogeneous in an excitation light propagation model.

12. The method of claim 1 further comprising determining autofluoresence data in the animal.

13. The method of claim 12 wherein the autofluoresence data determination includes forward modeling a tissue autofluoresence contribution to photon density at the surface portion.

14. The method of claim 13 further comprising altering the fluorescent light emission data with the autofluorescence data.

15. A method for obtaining a light distribution located inside an animal, the method comprising:
obtaining one or more fluorescent images of at least a portion of the animal;
obtaining a three dimensional representation of a surface portion of the animal;
dividing the three dimensional surface representation into a set of surface elements;
mapping fluorescent image data from the one or more fluorescent images to the set of surface elements to create fluorescent light emission data from the set of surface elements;
creating a set of volume elements within the animal;
converting the fluorescent light emission data from the set of surface elements into photon density internal to the animal using the set of surface elements and the set of volume elements;
determining a three-dimensional representation of a fluorescent probe distribution internal to the animal with a processor using the photon density internal to the animal and the set of volume elements; and
determining autofluoresence data in the animal,
wherein tissue in the animal is modeled as homogeneous in an excitation light propagation model.

16. The method of claim 15 wherein the autofluoresence data determination includes forward modeling a tissue autofluoresence contribution to photon density at the surface portion.

17. The method of claim 16 further comprising altering the fluorescent light emission data with the autofluorescence data.

18. The method of claim 15 further comprising:
dividing the surface portion into a set of surface elements;
dividing an interior of the animal into a set of volume elements; and
establishing a relationship between the set of surface elements and the set of volume elements.

19. The method of claim 15 wherein obtaining the one or more fluorescent images includes capturing an image of the animal with a camera while the animal rests on a horizontal surface.

20. A program storage device readable by a machine tangibly embodying a program of instructions executable by the machine to perform a method for obtaining a light distribution located inside an animal, the method comprising:
obtaining one or more fluorescent images of at least a portion of the animal;
obtaining a three dimensional representation of a surface portion of the animal;
dividing the three dimensional surface representation into a set of surface elements;
mapping fluorescent image data from the one or more fluorescent images to the set of surface elements to create fluorescent light emission data from the set of surface elements;
creating a set of volume elements within the animal;
converting the fluorescent light emission data from the set of surface elements into photon density internal to the animal using the set of surface elements and the set of volume elements; and
determining a three-dimensional representation of a fluorescent probe distribution internal to the animal using the photon density internal to the animal and the set of volume elements.

* * * * *

UNITED STATES PATENT AND TRADEMARK OFFICE
CERTIFICATE OF CORRECTION

PATENT NO. : 7,555,332 B2  Page 1 of 1
APPLICATION NO. : 11/829927
DATED : June 30, 2009
INVENTOR(S) : Rice et al.

It is certified that error appears in the above-identified patent and that said Letters Patent is hereby corrected as shown below:

In the Specification;

col. 4, line 23: "flourophores" -- has been changed to -- fluorophores --.

col. 4, line 23: "A flourophore" -- has been changed to -- A fluorophore --.

col. 20, lines 29 - 30: "mu(eff) = sqrt(3mu(A) (mu(A) + mu(S)) (13)" -- has been changed to -- mu(eff) = [3mu(A) (mu(A) + mu(S)] (13) --.

Signed and Sealed this

Eleventh Day of May, 2010

David J. Kappos
*Director of the United States Patent and Trademark Office*